(12) United States Patent
Huang et al.

(10) Patent No.: US 6,608,093 B2
(45) Date of Patent: Aug. 19, 2003

(54) PESTICIDAL 1-POLYARYLPYRAZOLES

(75) Inventors: Jamin Huang, Chapel Hill, NC (US); Scot Kevin Huber, Raleigh, NC (US)

(73) Assignee: Rhone-Poulenc Inc., Research Triangle Park, NC (US)

( * ) Notice: Subject to any disclaimer, the term of this patent is extended or adjusted under 35 U.S.C. 154(b) by 0 days.

(21) Appl. No.: 10/152,806

(22) Filed: May 23, 2002

(65) Prior Publication Data

US 2002/0193411 A1 Dec. 19, 2002

Related U.S. Application Data

(62) Division of application No. 09/832,861, filed on Apr. 12, 2001, now Pat. No. 6,433,002, which is a division of application No. 09/606,185, filed on Jun. 29, 2000, now Pat. No. 6,242,475, which is a division of application No. 09/216,878, filed on Dec. 21, 1998, now Pat. No. 6,107,322, which is a division of application No. 08/963,631, filed on Nov. 4, 1997, now Pat. No. 5,922,884.
(60) Provisional application No. 60/030,128, filed on Nov. 4, 1996.

(51) Int. Cl.$^7$ .................... A01N 43/653; C07D 249/08; C07D 249/12; C07D 249/14
(52) U.S. Cl. ....................... 514/340; 514/383; 514/384; 546/272.4; 548/263.8; 548/264.2; 548/265.6; 548/269.4
(58) Field of Search ............... 548/269.4, 263.8, 548/264.2, 265.6; 514/383, 384, 340; 546/272.4

(56) References Cited

U.S. PATENT DOCUMENTS

| | | | |
|---|---|---|---|
| 4,614,533 A | 9/1986 | Schallner et al. | 71/92 |
| 4,771,066 A | 9/1988 | Gehring et al. | 514/404 |
| 4,804,675 A | 2/1989 | Jensen-Korte et al. | 514/407 |
| 4,891,057 A | 1/1990 | Sohn et al. | 71/72 |
| 4,945,165 A | 7/1990 | Jensen-Korte et al. | 548/362 |
| 5,082,949 A | 1/1992 | Sohn et al. | 548/378 |
| 5,187,185 A | 2/1993 | Outcalt et al. | 514/408 |
| 5,223,525 A | 6/1993 | Wu et al. | 514/398 |
| 5,232,940 A | 8/1993 | Hatton et al. | 514/407 |
| 5,236,938 A | 8/1993 | Huang et al. | 514/341 |

FOREIGN PATENT DOCUMENTS

| | | |
|---|---|---|
| DE | 3633840 | 4/1988 |
| DE | 19511269 | 10/1995 |
| EP | 0154115 | 9/1985 |
| EP | 0201852 | 11/1986 |
| EP | 0235628 | 9/1987 |
| EP | 0285893 | 10/1988 |
| EP | 0295117 | 12/1988 |
| EP | 0385809 | 9/1990 |
| EP | 0403300 | 12/1990 |
| EP | 0500209 | 8/1992 |
| EP | 0679650 | 11/1995 |
| EP | 0780381 | 6/1997 |
| WO | 87/03781 | 7/1987 |
| WO | 93/06089 | 4/1993 |
| WO | 94/21606 | 9/1994 |
| WO | 96/25401 | 8/1996 |
| WO | 97/15555 | 5/1997 |

OTHER PUBLICATIONS

Khan et al., Chemical Abstracts, 78:72019, 1973.*
Grammaticakis, Chemical Abstracts, 75:35577, 1971, and C.R. Acad. Sc. Paris, Ser. C (1971), 272(18), pp. 1574–1577, published by Académie des sciences, Paris, France.
Melamed et al., Chemical Abstracts, 122:10820, 1995, and Tetrahedron Letters, vol. 35, No. 45, pp. 8329–8332 (1994), published by Pergamon Press, Oxford, England.
Hoelscher et al, Chemical Abstracts, 127:5092 (1997), published by American Chemical Society, Columbus, Ohio.
Perrin et al, Chemical Abstracts, 121:156825 (1994), published by American Chemical Society, Columbus, Ohio.

* cited by examiner

Primary Examiner—Fiona T. Powers
(74) Attorney, Agent, or Firm—Burns, Doane, Swecker & Mathis, L.L.P.

(57) ABSTRACT

A compound of formula (I):

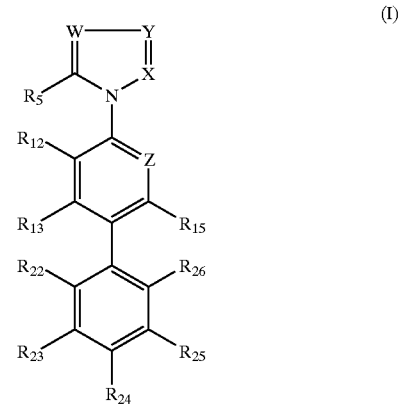

compositions containing them and methods of use to control pests.

40 Claims, No Drawings

PESTICIDAL 1-POLYARYLPYRAZOLES

CROSS-REFERENCE TO RELATED APPLICATIONS

This application is a divisional of U.S. patent application Ser. No. 09/832,861, filed Apr. 12, 2001, now U.S. Pat. No. 6,433,002, which is a divisional of U.S. patent application Ser. No. 09/606,185, filed Jun. 29, 2000, now U.S. Pat. No. 6,242,475, which is a divisional of U.S. patent application Ser. No. 09/216,878, filed Dec. 21, 1998, now U.S. Pat. No. 6,107,322, which is a divisional of U.S. patent application No. 08/963,631, filed Nov. 4, 1997, now U.S. Pat. No. 5,922,884, which claims the priority of U.S. Provisional Patent Application No. 60/030,128, filed Nov. 4, 1996. All five prior applications are incorporated by reference herein in their entireties and relied upon.

The invention relates to new 1-arylpyrazoles and derivatives thereof which have some valuable properties either as pesticides or as intermediates to make other pesticides. The invention further pertains to compositions of said compounds and methods, using said compounds either as intermediates to make other pesticides, or for the control of pests particularly insects, in particular to the application of said compounds or compositions in agricultural methods of use or for animal protection, particularly as pesticides, for controlling arthropods.

International Patent Publication No. WO 87/03781 and European Patent Publication No. 295117, 154115, 201852 describe insecticidal 1-(substituted phenyl) pyrazoles. Other prior art is also found in the text of these patent applications or the patents issued therefrom.

International Patent Publications No. WO 93/06089 and WO 94/21606 also describe insecticidal 1(4—$SF_5$ substituted phenyl) heterocycles which may be pyrroles as well as imidazoles or pyrazoles. The teaching of these patents is not substantially different from Iternational Patent Publication No. WO 87/03781 or from European Patent Publication No. 0295117 as far as pyrazoles are concerned.

It is an object of the present invention to provide new pesticidal compounds of the 1-arylpyrazole family together with processes for their preparation.

Another object of the present invention is to provide pesticidal compositions and pesticidal methods of use of the pesticidal pyrazole compounds against arthropods, especially insects, particularly in agricultural or horticultural crops, forestry, veterinary medicine or livestock husbandry, or in public health.

A third object of the present invention is to provide very active compounds with broad spectrum pesticidal activity, as well as compounds with selective special activity, e.g., aphicidal, miticidal, foliar insecticidal, soil insecticidal, systemic, antifeeding or pesticidal activity via seed treatment.

A fourth object of the present invention is to provide compounds with substantially enhanced and more rapid activity, especially against insects and more particularly insects in their larval stages.

A fifth objective of the present invention is to provide compounds with greatly improved (faster and greater) penetration into pest species when topically applied and to thus provide enhanced movement of the compounds to the pesticidal site(s) of action within the pest.

These and other objectives of the invention are met in whole or part and shall become readily apparent from the description of the present invention which follows.

The invention thus relates to compounds having the general formula (I):

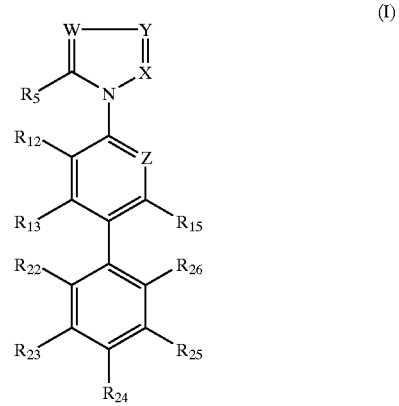

(I)

wherein:

X is N or C—$R_2$;

Y is N or C—$R_3$;

W is N or C—$R_4$;

$R_2$ and $R_3$ are independently selected from H, halogen, hydroxy, alkyl, cycloalkyl, haloalkyl, alkoxy, haloalkoxy, CN, $NO_2$, —$S(O)_nR_8$, alkylcarbonyl, alkoxycarbonyl, aminocarbonyl, alkylaminocarbonyl, dialkylaminocarbonyl, hydroxycarbonyl, aminosulfonyl, alkylaninosulfonyl, and dialkylaminosulfonyl;

$R_4$ is H, halogen, alkyl, alkoxy, CN, $NO_2$, haloalkyl, haloalkoxy, thiocyanato, formyl, alkylcarbonyl, —CH=N—OH, —CH=N—O-alkyl, —S($NH_2$)(=NH), —$S(O)_nR_8$, mercapto, haloalkylcarbonyl, or a —S— radical so that two molecules are bound together to form a disulfide compound;

$R_5$ is hydrogen, halogen, —$NR_9R_{10}$, —N=$CR_{11}R_{19}$, —$S(O)_nR_8$, formyl, alkylcarbonyl, haloalkylcarbonyl, cyano, alkyl, haloalkyl, hydrazino, alkoxycarbonyl, alkylthiocarbonyl, 1H-pyrrol-1-yl or 1H-pyrazol-1-yl;

$R_8$ is alkyl or haloalkyl, alkenyl or alkynyl, or a cycloalkyl ring containing 3 to 5 carbon atoms;

$R_{11}$ is H, or alkyl;

$R_{19}$ may also be hydrogen, alkyl, haloalkyl, alkoxy, haloalkoxy, alkylthio, amino, monoalkylamino, dialkylamino, or $R_{19}$ is phenyl, thienyl, pyridyl or furyl, each of which is unsubstituted or substituted with alkyl, haloalkyl, halogen, $NO_2$, CN, alkoxy, haloalkoxy, OH, alkylcarbonyl, alkylcarbonyloxy;

$R_9$ and $R_{10}$ independent of one another, are H, alkyl, haloalkyl, alkylcarbonyl, haloalkylcarbonyl, $R_8S(O)_n$, formyl, alkenyl, alkynyl, alkoxycarbonyl, alkylthiocarbonyl, aroyl; or are joined so as together form a divalent radical having 4 to 6 atoms in the chain, this divalent radical being alkylene, alkyleneoxyalkylene or alkyleneaminoalkylene, preferably to form a morpholine, pyrrolidine, piperidine or piperazine ring; the alkyl portion of $R_9$ and $R_{10}$ may be substituted by $R_7$;

$R_7$ is cyano, nitro, alkoxy, haloalkoxy, $R_8S(O)_n$, —C(O) alkyl, alkoxycarbonyl, aminocarbonyl, alkylaminocarbonyl, dialkylaminocarbonyl, —$CO_2H$, halogen, hydroxy, aminosulfonyl, alkylaminosulfonyl or dialkylaminosulfonyl;

Z is N or C—$R_{16}$;

n is zero, one or two;

$R_{12}$, $R_{13}$, $R_{15}$, $R_{16}$, are independently selected from hydrogen, halogen, alkyl, haloalkyl, cyanoalkyl, cyano, nitro, amino, hydrazino, alkoxy, haloalkoxy, alkylsulfenyl, alkylsulfinyl, alkylsulfonyl, haloalkylsulfenyl, haloalkylsulfinyl, haloalkylsulfonyl, formyl, alkylcarbonyl, alkoxycarbonyl;

$R_{22}$, $R_{23}$, $R_{24}$, $R_{25}$, $R_{26}$ are hydrogen, halogen, alkyl, haloalkyl, cyanoalkyl, cyano, nitro, amino, hydrazino, alkoxy, haloalkoxy, haloalkylcarbonyl, formyl, alkylcarbonyl, thioamide, amide, and alkoxycarbonyl, $SF_5$, $R_8S(O)_n$; preferably $R_{24}$ is halogen, haloalkyl or haloalkoxy; or $R_{22}$ and $R_{23}$ or $R_{23}$ and $R_{24}$ or $R_{25}$ and $R_{26}$ may also be together a divinylidene group (—CH=CH—CH=CH—) or a methylene diether (—O—CH$_2$—O—) or halomethylene diether (—O—CF$_2$—O—) so as to form a cyclic ring vicinal to the phenyl ring; or pesticidally acceptable salts thereof.

By the term "pesticidally acceptable salts" is meant salts the anions and cations of which are known and accepted in the art for the formation of pesticidally acceptable salts. Preferably such salts are water soluble. Suitable acid addition salts formed from compounds of formula (I) containing an amine group, include salts with inorganic acids for example hydrochlorides, phosphates, sulfates and nitrates, and salts with organic acids for example acetates. Suitable salts with bases formed from compounds of formula (I) containing a suitably acidic group include alkali metal (for example sodium or potassium) salts, ammonium salts and organic amine (for example diethanolamine or morpholine) salts.

In the present invention, some words are used in a specific sense:

The term "lower alkyl—$S(O)_n$" means a radical of the formula —$S(O)_n$— lower alkyl. The term "$R_{10}S(O)_n$" means a radical of the formula —$S(O)_nR_{10}$. The term "aminocarbonyl" means a carbamoyl radical, that is, a radical of the formula —C(O)NH$_2$. Similarly, the term "alkylaminocarbonyl" means an alkylcarbamoyl radical, that is, a radical of the formula —C(O)—NH-alkyl; and the term "dialkylaminocarbonyl" means a dialkylcarbamoyl radical, that is, a radical of the formula —C(O)—N(alkyl)$_2$ in which the alkyl moieties can be the same or different. The term "aminosulfonyl" means a sulfamoyl radical, that is, —SO$_2$NH$_2$. Similarly, the term "alkylaminosulfonyl" means an alkylsulfamoyl radical, that is, a radical of the formula —SO$_2$NH-alkyl; while the term "dialkylaminosulfonyl" means a dialkylsulfamoyl radical, which has the formula —SO$_2$N(alkyl)$_2$ wherein the alkyl moieties can be the same or different.

The term "halo" before the name of a radical means that this radical is partially or completely halogenated, that is to say, substituted by F, Cl, Br, or I, in any combination, preferably by F or Cl. The term "halogen" means F, Cl, Br or I. The term "lower" before the name of a radical having a carbon skeleton means that this carbon skeleton has less than 6 carbon atoms. When the name of any substituent is repeated, it keeps the same meaning unless otherwise specified. The term "aryl" designates a carbon and/or heteroatom-containing aromatic radical which is preferably phenyl optionally substituted with one or more substituents selected from halogen, methyl and methoxy, especially phenyl, halophenyl, tolyl or xylyl. The term "aroyl" designates a carbonyl aromatic radical, that is, aryl—C(O)—, which is preferably a benzoyl, methylbenzoyl, halobenzoyl or xylylcarbonyl radical. The term "acyl" designates an alkylcarbonyl radical. The various individual radicals (such as alkyl, alkenyl, alkynyl, alkoxy and alkylene or the like) generally contain up to six carbon atoms.

A preferred class of compounds of formula (I) is that wherein

X is N;

Y is C—$R_3$;

W is C—$R_4$;

$R_3$ is H, halogen, hydroxy, alkyl, cycloalkyl, haloalkyl, alkoxy, haloalkoxy, CN, NO$_2$, —$S(O)_nR_8$, alkylcarbonyl, alkoxycarbonyl, aminocarbonyl, alkylaminocarbonyl, dialkylaminocarbonyl, hydroxycarbonyl, aminosulfonyl, alkylaminosulfonyl, dialkylaminosulfonyl;

$R_4$ is H, halogen, alkyl, alkoxy, CN, NO$_2$, haloalkyl, haloalkoxy, thiocyanato, formyl, alkylcarbonyl, —CH=N—OH, —CH=N—O-alkyl, —S(NH$_2$)(=NH), —$S(O)_nR_8$, mercapto, haloalkylcarbonyl, or a —S— radical so that two molecules are bound together to form a disulfide compound;

$R_5$ is hydrogen, halogen, —NR$_9$R$_{10}$, —N=CR$_{11}$R$_{19}$, —$S(O)_nR_8$, formyl, alkylcarbonyl, haloalkylcarbonyl, cyano, lower alkyl, hydrazino, alkoxycarbonyl, alkylthiocarbonyl, 1H-pyrrol-1-yl or 1H-pyrazol-1-yl, preferably, amino —NR$_9$R$_{10}$;

$R_8$ is alkyl or haloalkyl, alkenyl or alkynyl; or a cycloalkyl ring containing 3 to 5 carbon atoms; preferably $R_8$ is lower alkyl;

$R_{11}$ is H or alkyl;

$R_{19}$ may also be hydrogen, alkyl, haloalkyl, alkoxy, haloalkoxy, alkylthio, amino, monoalkylamino, dialkylamino;

or $R_{19}$ is phenyl, thienyl, pyridyl or furyl, all of them being optionally substituted with alkyl, haloalkyl, halogen, NO$_2$, CN, alkoxy, haloalkoxy, OH, alkylcarbonyl, alkylcarbonyloxy;

$R_9$ and $R_{10}$ are H, alkyl, haloalkyl, alkylcarbonyl, haloalkylcarbonyl, $R_8$—$S(O)_n$, formyl, alkenyl, alkynyl, alkoxycarbonyl, alkylthiocarbonyl, aroyl; or are joined so as together form a divalent radical having 4 to 6 atoms in the chain, this divalent radical being alkylene, alkyleneoxyalkylene or alkyleneaminoalkylene, preferably to form a morpholine, pyrrolidine, piperidine or piperazine ring; the alkyl portion of $R_9$ and $R_{10}$ may be substituted by $R_7$;

$R_7$ is cyano, nitro, alkoxy, haloalkoxy, $R_8S(O)_n$, —C(O) alkyl, alkoxycarbonyl, aminocarbonyl, alkylaminocarbonyl, dialkylaminocarbonyl, —CO$_2$H, halogen, hydroxy, aminosulfonyl, alkylaminosulfonyl or dialkylaminosulfonyl;

Z is N or C—$R_{16}$;

n is zero, one or two;

$R_{12}$, $R_{13}$, $R_{15}$, $R_{16}$, are separately hydrogen, halogen, alkyl, haloalkyl, cyanoalkyl, cyano, nitro, amino, hydrazino, alkoxy, haloalkoxy, alkylsulfenyl, alkylsulfinyl, alkylsulfonyl, haloalkylsulfenyl, haloalkylsulfinyl, haloalkylsulfonyl, formyl, alkylcarbonyl, alkoxycarbonyl;

$R_{22}$, $R_{23}$, $R_{24}$, $R_{25}$, $R_{26}$ are hydrogen, halogen, alkyl, haloalkyl, cyanoalkyl, cyano, nitro, amino, hydrazino, alkoxy, haloalkoxy, haloalkylcarbonyl, formyl, alkylcarbonyl, thioamide, amide, and alkoxycarbonyl, $SF_5$, $R_8S(O)_n$, preferably, $R_{24}$ is halogen, haloalkyl or haloalkoxy; or $R_{22}$ and $R_{23}$ or $R_{23}$ and $R_{24}$ or $R_{25}$ and $R_{26}$ may also be together a divinylidene group (—CH=CH—CH=CH—) or a methylene diether (—O—CH$_2$—O—) or halomethylene diether (—O—CF$_2$—O—) so as to form a cyclic ring vicinal to the phenyl ring; or a pesticidally acceptable salt thereof.

Another preferred class of the compounds of formula (I) are those with one or more of the following features wherein:

X is N or C—R$_2$;

Y is N or C—R$_3$;

W is N or C—R$_4$;

R$_3$ is CN or halogen;

R$_4$ is H, halogen, formyl, or —S(O)$_n$R$_8$;

R$_5$ is hydrogen, halogen, C$_1$–C$_3$ alkyl, C$_1$–C$_3$ haloalkyl, or —NR$_9$R$_{10}$;

R$_8$ is methyl, ethyl, —CF$_3$, —CFCl$_2$, —CF$_2$Cl;

R$_{12}$ and R$_{16}$ are independently selected from F, Cl, Br and H;

R$_{13}$ and R$_{15}$ are H;

R$_{24}$ is —CF$_3$, —OCF$_3$, —CHF$_2$, —S(O)$_n$CF$_3$, —CFCl$_2$, —CF$_2$Cl, —OCF$_2$Cl, —OCFCl$_2$, Cl, Br or F; or

Z is CCl, CF, CBr or N.

A further especially preferred class of compounds are those wherein:

X is N;

Y is C—R$_3$;

W is C—R$_4$;

R$_{12}$ and R$_{16}$ are Cl or Br;

R$_{13}$ and R$_{15}$ are H;

R$_{24}$ is —CF$_3$, —OCF$_3$ or Br;

R$_5$ is amino;

R$_9$ and R$_{10}$ are H, alkyl or alkylcarbonyl;

R$_8$ is methyl or ethyl or CF$_3$, CCl$_2$F, CClF$_2$; and

R$_3$ is CN or halogen.

For the above preferred compounds, there are optimum combinations of substituent groups.

Further, preferred S(O)$_n$R$_8$ substituents in formula (I) are: methylthio, methylsulfinyl, methylsulfonyl, ethylsulfinyl, ethylsulfonyl, ethylthio, cyclopropylsulfinyl, cyclopropylthio, cyclopropylsulfonyl, isopropylsulfinyl, isopropylsulfonyl, isopropylthio, trifluoromethylthio, trifluoromethylsulfinyl, trifluoromethylsulfonyl, dichlorofluoromethylthio, dichloromethylsulfinyl, dichloromethylsulfonyl, chlorodifluoromethylthio, chlorodifluoromethylsulfonyl or chlorodifluoromethylsulfinyl.

Some compounds are useful as intermediates to make other pesticides, others are useful directly as pesticides. Compounds wherein R$_{23}$ or R$_{24}$ or R$_{25}$ is formyl are preferred as intermediates as well as compounds wherein R$_5$ is H or compounds wherein simultaneously R$_4$ is not halogenated and R$_{22}$ and R$_{23}$ and R$_{24}$ and R$_{25}$ and R$_{26}$ are H.

The compounds of general formula (I) can be prepared by the application or adaptation of known methods (i.e., methods heretofore used or described in the chemical literature including the *Chemical Abstracts*) employing as starting material the compounds of formula (II)

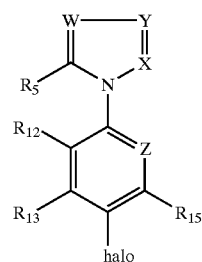

wherein the various substituents have the same meaning as in formula (I) and halo is a halogen atom, preferably bromine or iodine.

The compounds of formula (II) can be prepared by methods or processes similar to those described in International patent applications WO 87/03781, 93/06089, 94/21606, in European patent applications 295117, 403300, 385809, 500209, 679650, 285,893, and 780,381, U.S. Pat. Nos. 5,232,940, 5,236,938, 5,187,185, 5,223,525 and German Patent application 19511269 or by other methods known to the skilled addressee. The skilled addressee understands and is generally knowledgeable of Chemical Abstracts.

According to a first method of preparation of compounds of formula (I) from compounds of formula (II), a compound of formula (II) is caused to react with a boric acid or ester, preferably in presence of a coupling catalyst, so as to form a compound of formula (III)

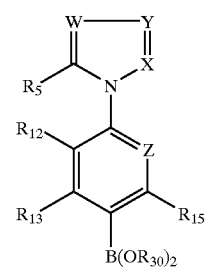

wherein the substituents have the same meaning as previously indicated, and B(OR$_{30}$)$_2$ represents a boric acid or ester group (R$_{30}$ is preferably hydrogen, alkyl, or a divalent lower alkylene radical such that two R$_{30}$O radicals may form a cyclic borate ester), said compound (III) being, in a second step, caused to react with a compound of formula (VI)

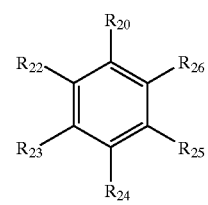

wherein R$_{20}$ is bromine or iodine or O—SO$_2$CF$_3$.

The first step of this first process is generally and preferably conducted in an organic solvent, for example an hydrocarbon such as toluene or xylene; an amide such as dimethylformamide or N-methylpyrrolidone; an ether such as tetrahydrofuran, dimethoxyethane or 2-methoxyethylether; the temperature is generally between 50° C. and 150° C.; utilizing as catalysts organic derivatives of palladium including palladium acetate, tetrakis(triphenylphosphine) palladium(O) or $Pd_2$ (dibenzylidene acetone)$_3$, generally in the presence of a base such as an alkaline hydroxide or carbonate acetate ion or an amine. The boron derivative used as a reactant with the compound of formula (II) is preferably a cyclic diboron ester or acid of formula $(R_{30}O)_2B$—$B(OR_{30})_2$.

The second step of this first process is advantageously conducted in an organic solvent, for example an hydrocarbon such as toluene or xylene; an amide such as dimethylformamide or N-methylpyrrolidone; an ether such as tetrahydrofuran, dimethoxyethane or 2-methoxyethylether; the temperature is generally between 50° C. and 150° C.; utilizing as catalysts organic derivatives of palladium including palladium acetate, tetrakis(triphenylphosphine) palladium(O) or $Pd_2$ (dibenzylidene acetone)$_3$, generally in the presence of a base such as an alkaline hydroxide or carbonate acetate ion or an amine.

According to another method of preparation of compound of formula (I), a compound of formula (II) is caused to react with a compound of formula (IV):

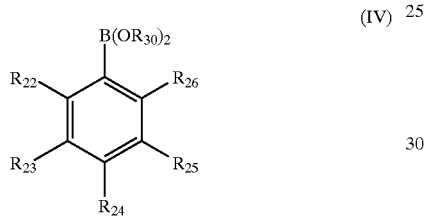

(IV)

wherein the substituents have the same meaning as previously indicated.

The process is generally and preferably conducted in an organic solvent, for example an hydrocarbon such as toluene or xylene; an amide such as dimethylformamide or N-methylpyrrolidone; an ether such as tetrahydrofuran, dimethoxyethane or 2-methoxyethylether; the temperature is generally between 50° C. and 150° C.; utilizing as catalysts organic derivatives of palladium including palladium acetate, tetrakis(triphenylphosphine)palladium(O) or $Pd_2$ (dibenzylidene acetone)$_3$, generally in the presence of a base such as an alkaline hydroxide or carbonate acetate ion or an amine.

According to still another method of preparation of compound of formula (I), a compound of formula (II) is caused to react in the presence of a catalyst as described above, with a hexaalkylstannane [(alkyl or cycloalkyl)$_3$Sn]$_2$ so as to form a compound of formula (V):

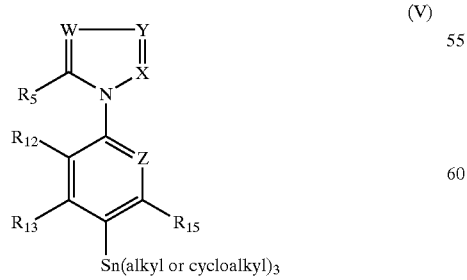

(V)

which in a second step is caused to react with a compound of formula (IV) in the presence of a coupling catalyst.

The first step of the process is generally conducted in an organic solvent, for example an hydrocarbon such as toluene or xylene; an amide such as dimethylformamide or N-methylpyrrolidone; an ether such as tetrahydrofuran, dimethoxyethane or 2-methoxyethylether, at a temperature generally between 50° C. and 150° C.; utilizing as catalysts organic derivatives of palladium including palladium acetate, tetrakis(triphenylphosphine)palladium(O) or $Pd_2$ (dibenzylidene acetone)$_3$.

The second step of this second process is generally conducted in an organic solvent, for example an hydrocarbon such as toluene or xylene; an amide such as dimethylformamide or N-methylpyrrolidone; an ether such as tetrahydrofuran, dimethoxyethane or 2-methoxyethylether; the temperature is generally between 50° C. and 150° C.; as catalysts, organic derivatives of palladium such as Pd (P-phenyl$_3$)$_4$, Pd$_2$ (dibenzylidene acetone)$_3$, Pd (O—CO—CH$_3$)$_2$ may be cited.

According to still another method of preparation of compound of formula (I), a compound of formula (II) is caused to react with a compound of formula (VII)

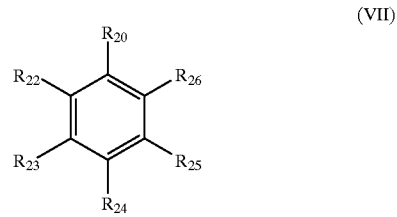

(VII)

preferably in the presence of a coupling catalyst as described above, and preferably in a solvent as described above, and preferably at a temperature from 50° C. to 150° C.

According to another method of preparation of a compound of formula (I), a compound of formula (VIII):

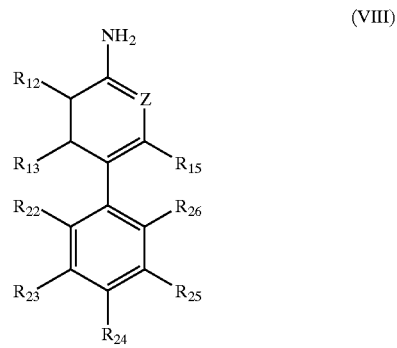

(VIII)

is reacted in a step to form a pyrrole, imidazole, triazole, or pyrazole of formula (I). Such reactions are known and can be found in Katritzky, Rees, and Scriven, *Comprehensive Heterocyclic Chemistry II, volumes 2.3.4* 1996, Pergamon Press, London.

The invention is illustrated by the following examples, which are not considered as limiting the invention but are given to better enable use of it.

EXAMPLE 1

Preparation of 1-[2,6-dichloro-4-(4-trifluoromethylphenyl)phenyl]-3-cyano-4-trifluoromethylthio-5-aminopyrazole A mixture of 6 g of 5-amino-3-cyano-1-(2,6-dichloro-4-bromophenyl)-4-trifluoromethylthiopyrazole (prepared according to procedures reported in U.S. Pat. No. 5,232, 940), 4-trifuoromethylphenylboronic acid (5.3 g), $K_2CO_3$ (5.8 g), tris-(dibenzylidene acetone) dipalladium (0.6 g) and diglyme was heated at 130° C. for 25 hours. After cooling to 20° C., the mixture was poured into water and extracted with diethyl ether. The ether solutions were combined, dried, filtered and the filtrate concentrated and purified by chromatography. The desired product as a solid (3.9 g, mp 181–184° C.) was obtained.

EXAMPLE 2

Preparation of 1-[2,6-dichloro-4-(4trifluoromethylphenyl)phenyl]-3-cyano-4-trifluoromethylsulfonyl-5-aminopyrazole A solution of 1-[2,6dichloro-4-(trifluoromethylphenyl) phenyl]-3-cyano-4-trifluoromethylthio-5-aminopyrazole (0.5 g), m-chloroperbenzoic acid (2.2 g) and 1,2-dichloroethane was heated at reflux for 40 hours. After cooling to 20° C., the mixture was dissolved in diethyl ether and washed with sat, aqueous $NaHCO_3$ solution twice, then saturated aqueous $NaHSO_3$ solution twice, dried, filtered, and the filtrate concentrated and purified by chromatography. The desired product as a solid (0.13 g, mp 197–202° C.) was obtained.

EXAMPLE 3

Preparation of 1-[2,6dichloro-4-(tributyltin)phenyl]-3-cyano-4-trifluoromethylthio-5-aminopyrazole A mixture of 1-(2,6-dichloro4-bromophenyl)-3-cyano-4-trifluoromethylthio-5-aminopyrazole (5 g), bis-(tributyltin) (6.7 g), tetrakis(tri-phenylphosphine)palladium (O) (1.3 g) and 1-methyl-2-pyrrolidinone was heated to reflux for 75 minutes, cooled to 20° C., poured to water and extracted with methyl t-butyl ether. After concentrattion to dryness, methylene chloride was added and stirred with saturated aqueous KF solution for 16 hours. More water was added and extracted with methylene chloride. The methylene chloride solutions were combined, dried, filtered and the filtrate concentrated and purified via chromatography. The desired product as a solid (1.9 g, mp 116–117° C.) was obtained.

EXAMPLE 4

Preparation of 1-[2,6-dichloro4-(2,3,5,6-tetrafluoropyrid4-yl)phenyl]-3-cyano-4-trifluoromethylthio-5-aminopyrazole A mixture of 1-[2,6-dichloro-4-(tributyltin)phenyl]-3-cyano-4-trifluoromethylthio-5-aminopyrazole (0.5 g), 4-bromo-2,3,5,6-tetrafluoropyridine (0.1 mL), tetrakis(triphenylphosphine) palladium (O) (0.1 g) and THF was refluxed for 26 hours. After cooling to 20° C., methylene chloride was added and stirred with saturated aqueous KF solution for 16 hours. The mixture was filtered with diethyl ether and dried, filtered again and the filtrate concentrated and purified via chromatography. The desired product as a solid (87 mg, mp 100–104° C.) was obtained.

EXAMPLE 5

Preparation of 1-[2,6-dichloro-4-(4trifluoromethylphenyl)phenyl]-3-cyano-5-aminopyrazole.

A mixture of 1-(2,6-dichloro-4-bromophenyl)-3-cyano-5-aminopyrazole (45 g, prepared according to procedures reported in U.S. Pat. No. 5,232,940), 4-trifluoromethylphenylboronic acid (45 g), 2 M of $Na_2CO_3$ (75 mL), tris-(dibenzylideneacetone) dipalladium (6.4 g), toluene and ethanol was heated at 130° C. for 25 hours. After cooling to 20° C., the mixture was poured into water and extracted with diethyl ether. The ether solutions were combined, dried, filtered and the filtrate concentrated and purified via chromatography. The desired product as a solid (30.6 g, mp 195–199° C.) was obtained.

EXAMPLE 6

Preparation of 1-[2,6-dichloro-4-(4-trifluoromethylphenyl)phenyl]-3-cyano4-bromo-5-aminopyrazole.

A mixture of 1-[2,6-dichloro-4-(4-trifluoromethylphenyl) phenyl]-3-cyano-5-aminopyrazole (1 g), N-bromosuccinimide (0.5 g) and acetonitrile was stirred at 20° C. for 90 minutes, then concentrated and the residue was mixed with diethyl ether, washed with saturated aqueous $NaHCO_3$ solution, dried, filtered and the filtrate concentrated and purified via chromatography. The desired product as a solid (1.04 g, mp 178–180° C.) was obtained.

EXAMPLE 7

Preparation of 4-dichlorofluoromethylsulfenyl-1-[2-fluoro-4-(4-trifluoromethylphenyl) phenyl]imidazole Step A A solution of 4-bromo-2-fluoroaniline (3.8 g) in 20 ml of triethyl orthoformate was stirred at room temperature. After stirring for 1 h, tetrahydrofuran (40 ml), aminoacetonitrile hydrochloride (2.8 g), and diisopropylamine (5.3 ml) were added and stirring continued for an additional hour. After 1 h, the mixture was poured into 150 ml of ice water and extracted with 150 ml of dichloromethane. The organic solution was washed twice with water and dried over magnesium sulfate. Evaporation of solvents afforded a light purple solid (3.1 g), which was washed with hexane and filtered.

The solid was dissolved in 40 ml of dichloromethane at reflux, cooled to room temperature, and treated with tetramethylguanidine (1.6 ml), added dropwise over twenty minutes. After stirring at room temperature overnight, the mixture was cooled in an ice/salt bath and dichlorofluoromethylsulfenyl chloride (1.5 ml) was added. After 1 h, the mixture was diluted with 100 ml of methylene chloride and washed with saturated sodium bicarbonate solution, then with water, then dried over magnesium sulfate. After filtration and evaporation, chromatography on silica gel afforded 5-amino-4-dichlorofluoromethylsulfenyl-1-(2-fluoro-4-bromophenyl)imidazole (1.285 g).

Step B 1 g of 5-amino-4-dichlorofluoromethylsulfenyl-1-(2-fluoro-4-bromophenyl) imidazole was dissolved in 15 ml of tetrahydrofuran, cooled to 0° C., and treated with t-butylnitrite. After 1 h, the mixture is evaporated. Silca gel chromatography afforded 4-dichlorofluoromethylsulfenyl-1-(2-fluoro-4-bromophenyl)imidazole (0.555 g).

Step C 50 mg of 4-dichlorofluoromethylsulfenyl-1-(2-fluoro-4-bromophenyl)imidazole and 37 mg of trifluoromethylphenylboronic acid in 3 ml of toluene were treated with 0.13 ml of 2 M aqueous potassium carbonate and a catalytic amount (about 5 mg) of palladium tetrakis(triphenylphosphine). The mixture was heated at 90° C. for 12 h, then cooled to room temperature and evaporated. Silica gel chromatography afforded 4-dichlorofluoromethylsulfenyl-1-[2-fluoro-4-(4-trifluoromethylphenyl)phenyl]imidazole (27.3 mg, mass spec m/e 438).

In a manner similar to that employed in examples 1 to 7, the following compounds in Tables 1–4 were also prepared. The last column of the table indicates the physical characteristic of the compound obtained from the mass spectrum analysis. It is the m/e value from the mass spectrum of the molecular ion. The number of the compound is for identification only.

N/A=Not Applicable

AroCH is [4—OH 3-methoxy phenyl]—CH, so that AroCH=N— is the group [4—OH 3-methoxy phenyl]—CH=N—

TABLE 1

| CMP.NO | R12 | R13 | R15 | R16 | R22 | R23 | R24 | R25 | R26 | R3 | R4 | R5 | m/e |
|---|---|---|---|---|---|---|---|---|---|---|---|---|---|
| 1 | Cl | H | H | Cl | (CH=CH)2 | | H | H | H | CN | SCF3 | NH2 | 478 |
| 2 | Cl | H | H | Cl | H | H | H | H | H | CN | SCF3 | NH2 | 428 |
| 3 | Cl | H | H | Cl | Me | H | H | H | H | CN | SCF3 | NH2 | 442 |
| 4 | Cl | H | H | Cl | H | NH2 | H | H | H | CN | SCF3 | NH2 | 443 |
| 5 | Cl | H | H | Cl | H | NO2 | H | H | H | CN | SCF3 | NH2 | 473 |
| 6 | Cl | H | H | Cl | H | NHAc | H | H | H | CN | SCF3 | NH2 | 485 |
| 7 | Cl | H | H | Cl | H | CHO | H | H | H | CN | SCF3 | NH2 | 456 |
| 8 | Cl | H | H | Cl | H | H | OMe | H | H | CN | SCF3 | NH2 | 458 |
| 9 | Cl | H | H | Cl | H | H | SMe | H | H | CN | SCF3 | NH2 | 474 |
| 10 | Cl | H | H | Cl | H | H | F | H | H | CN | SCF3 | NH2 | 446 |
| 11 | Cl | H | H | Cl | H | F | H | H | H | CN | SCF3 | NH2 | 446 |
| 12 | Cl | H | H | Cl | H | Cl | F | H | H | CN | SCF3 | NH2 | 480 |
| 13 | Cl | H | H | Cl | H | H | Cl | H | H | CN | SCF3 | NH2 | 462 |
| 14 | Cl | H | H | Cl | H | H | Br | H | H | CN | SCF3 | NH2 | 506 |
| 15 | Cl | H | H | Cl | H | Cl | H | Cl | H | CN | SCF3 | NH2 | 496 |
| 16 | Cl | H | H | Cl | H | H | CF3 | H | H | CN | SCF3 | NH2 | 496 |
| 17 | Cl | H | H | Cl | H | CF3 | H | CF3 | H | CN | SCF3 | NH2 | 564 |
| 18 | Cl | H | H | Cl | (CH=CH)2 | | H | H | H | CN | SMe | NH2 | 424 |
| 19 | Cl | H | H | Cl | H | H | H | H | H | CN | SMe | NH2 | 374 |
| 20 | Cl | H | H | Cl | Me | H | H | H | H | CN | SMe | NH2 | 388 |
| 21 | Cl | H | H | Cl | H | NH2 | H | H | H | CN | SMe | NH2 | 389 |
| 22 | Cl | H | H | Cl | H | NO2 | H | H | H | CN | SMe | NH2 | 419 |
| 23 | Cl | H | H | Cl | H | NHAc | H | H | H | CN | SMe | NH2 | 431 |
| 24 | Cl | H | H | Cl | H | H | CHO | H | H | CN | SMe | NH2 | 402 |
| 25 | Cl | H | H | Cl | H | H | OMe | H | H | CN | SMe | NH2 | 404 |
| 26 | Cl | H | H | Cl | H | F | H | H | H | CN | SMe | NH2 | 392 |
| 27 | Cl | H | H | Cl | H | Cl | F | H | H | CN | SMe | NH2 | 426 |
| 28 | Cl | H | H | Cl | Cl | H | Cl | H | H | CN | SMe | NH2 | 442 |
| 29 | Cl | H | H | Cl | H | H | CF3 | H | H | CN | SMe | NH2 | 442 |
| 30 | Cl | H | H | Cl | H | CF3 | H | CF3 | H | CN | SMe | NH2 | 510 |
| 31 | Cl | H | H | Cl | H | Br | H | H | H | CN | SMe | NH2 | 452 |
| 32 | Cl | H | H | Cl | Me | H | H | H | H | CN | SCF3 | Van-CH=N— | 576 |
| 33 | Cl | H | H | Cl | H | NO2 | H | H | H | CN | SCF3 | Van-CH=N— | 607 |
| 34 | Cl | H | H | Cl | H | NHAc | H | H | H | CN | SCF3 | Van-CH=N— | 619 |
| 35 | Cl | H | H | Cl | H | H | CHO | H | H | CN | SCF3 | Van-CH=N— | 590 |
| 36 | Cl | H | H | Cl | H | H | OMe | H | H | CN | SCF3 | Van-CH=N— | 592 |
| 37 | Cl | H | H | Cl | H | Cl | F | H | H | CN | SCF3 | Van-CH=N— | 614 |
| 38 | Cl | H | H | Cl | Cl | H | Cl | H | H | CN | SCF3 | Van-CH=N— | 630 |
| 39 | Cl | H | H | Cl | H | H | CF3 | H | H | CN | SCF3 | Van-CH=N— | 630 |
| 40 | Cl | H | H | Cl | H | H | CF3 | H | H | CN | S(O)2CCl2F | NH2 | 560 |
| 41 | Cl | H | H | Cl | H | H | CF3 | H | H | CN | S(O)2CCl2F | NH2 | 544 |
| 42 | Cl | H | H | Cl | H | H | CF3 | H | H | CN | SCCl2F | NH2 | 528 |
| 43 | Cl | H | H | Cl | H | H | CF3 | H | H | CN | SOCF3 | NH2 | 512 |
| 44 | Cl | H | H | Cl | H | H | CF3 | H | H | CN | S(O)2CF3 | NH2 | 528 |
| 45 | Cl | H | H | Cl | H | H | CF3 | H | H | PhC(O) | SCF3 | NH2 | 575 |
| 46 | Cl | H | H | Cl | (CH=CH)2 | | H | H | H | CN | SCF3 | H | 463 |
| 47 | Cl | H | H | Cl | H | (CH=CH)2 | | H | H | CN | SCF3 | H | 463 |
| 48 | Cl | H | H | Cl | H | H | H | H | H | CN | SCF3 | H | 413 |
| 49 | Cl | H | H | Cl | H | NO2 | H | H | H | CN | SCF3 | H | 458 |
| 50 | Cl | H | H | Cl | H | H | OMe | H | H | CN | SCF3 | H | 443 |
| 51 | Cl | H | H | Cl | H | H | SMe | H | H | CN | SCF3 | H | 459 |
| 52 | Cl | H | H | Cl | H | H | F | H | H | CN | SCF3 | H | 431 |
| 53 | Cl | H | H | Cl | H | F | H | H | H | CN | SCF3 | H | 431 |
| 54 | Cl | H | H | Cl | H | Cl | F | H | H | CN | SCF3 | H | 465 |
| 55 | Cl | H | H | Cl | H | H | Cl | H | H | CN | SCF3 | H | 447 |
| 56 | Cl | H | H | Cl | H | H | Br | H | H | CN | SCF3 | H | 491 |
| 57 | Cl | H | H | Cl | H | Cl | H | Cl | H | CN | SCF3 | H | 481 |
| 58 | Cl | H | H | Cl | Cl | H | Cl | H | H | CN | SCF3 | H | 481 |

TABLE 1-continued

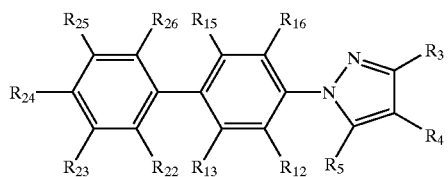

| CMP.NO | R12 | R13 | R15 | R16 | R22 | R23 | R24 | R25 | R26 | R3 | R4 | R5 | m/e |
|---|---|---|---|---|---|---|---|---|---|---|---|---|---|
| 59 | Cl | H | H | Cl | H | H | CF3 | H | H | CN | SCF3 | H | 481 |
| 60 | Cl | H | H | Cl | H | CF3 | H | H | H | CN | SCF3 | H | 481 |
| 61 | Cl | H | H | Cl | H | CF3 | H | CF3 | H | CN | SCF3 | H | 549 |
| 62 | Cl | H | H | Cl | H | H | Cl | H | H | CN | SCF3 | H | 447 |
| 63 | Cl | H | H | Cl | H | Br | H | H | H | CN | SCF3 | H | 491 |
| 64 | Cl | H | H | Cl | H | H | CF3 | H | H | PhC(O) | S(O)2CCl2F | NH2 | 639 |
| 65 | Cl | H | H | Cl | H | H | Br | H | H | CN | SCCl2F | NH2 | 538 |
| 66 | Cl | H | H | Cl | Cl | H | CF3 | H | Cl | CN | SCF3 | NH2 | 564 |
| 67 | Cl | H | H | Cl | H | H | OCF3 | H | H | CN | SCF3 | NH2 | 512 |
| 68 | Cl | H | H | Cl | H | H | CF3 | H | H | PhC(O) | S(O)2CClF2 | NH2 | 623 |
| 69 | Cl | H | H | Cl | H | H | CF3 | H | H | CN | H | NH2 | 396 |
| 70 | Cl | H | H | Cl | H | H | CF3 | H | H | CN | Br | NH2 | 474 |
| 71 | Cl | H | H | Cl | H | H | CF3 | H | H | CN | SEt | NH2 | 456 |
| 72 | Cl | H | H | Cl | H | H | CF3 | H | H | CN | SMe | NH2 | 442 |
| 73 | Cl | H | H | Cl | H | H | CF3 | H | H | CN | SCN | NH2 | 453 |
| 74 | Cl | H | H | Cl | H | H | CF3 | H | H | CN | Cl | NH2 | 430 |
| 75 | Cl | H | H | Cl | H | H | CF3 | H | H | CN | SOMe | NH2 | 458 |
| 76 | Cl | H | H | Cl | H | H | CF3 | H | H | CN | S(O)Et | NH2 | 472 |
| 77 | Cl | H | H | Cl | H | H | Br | H | H | CN | S(O)2CCl2F | NH2 | 570 |
| 78 | Cl | H | H | Cl | H | H | CF3 | H | H | CN | S(O)2CH3 | NH2 | 474 |
| 79 | Cl | H | H | Cl | H | H | CF3 | H | H | CN | S(O)2Et | NH2 | 488 |
| 80 | Cl | H | H | Cl | H | H | CF3 | H | H | CONH2 | C(OH)(CF3)2 | NH2 | 580 |
| 81 | Cl | H | H | Cl | H | H | CF3 | H | H | CN | C(OH)(CF3)2 | NH2 | 562 |
| 82 | Cl | H | H | Cl | H | H | CF3 | H | H | CN | H | NHAc | 438 |
| 83 | Cl | H | H | Cl | H | H | CF3 | H | H | Ac | SMe | NH2 | 459 |
| 84 | Cl | H | H | Cl | H | H | CF3 | H | H | CN | CF(CF3)2 | NH2 | 564 |
| 85 | Cl | H | H | Cl | H | H | CF3 | H | H | CN | SCCl2F | H | 513 |
| 86 | Cl | H | H | Cl | H | H | CF3 | H | H | CN | S(O)2CCl2F | H | 545 |
| 87 | Cl | H | H | Cl | H | Cl | Cl | H | H | CN | H | NH2 | 396 |
| 88 | Cl | H | H | Cl | H | H | OCF3 | H | H | CN | H | NH2 | 412 |
| 89 | Cl | H | H | Cl | H | F | H | H | H | CN | H | NH2 | 346 |
| 90 | Cl | H | H | Cl | H | H | CO2Me | H | H | CN | H | NH2 | 386 |
| 91 | Cl | H | H | Cl | H | Cl | Cl | H | H | CN | SCF3 | NH2 | 496 |
| 92 | Cl | H | H | Cl | F | H | H | H | H | CN | SCF3 | NH2 | 446 |
| 93 | Cl | H | H | Cl | H | H | CO2Me | H | H | CN | SCF3 | NH2 | 486 |
| 94 | Cl | H | H | Cl | H | H | CF3 | H | H | CN | SCCl2F | Br | 591 |
| 95 | Cl | H | H | Cl | H | H | CF3 | H | H | Ac | S(O)2CH3 | NH2 | 491 |
| 96 | Cl | H | H | Cl | Cl | H | H | H | Cl | CN | SCF3 | NH2 | 496 |
| 97 | Cl | H | H | Cl | Cl | H | Cl | H | H | CN | SCF3 | NH2 | 496 |
| 98 | Cl | H | H | Cl | Cl | H | CF3 | H | Cl | CN | SCF3 | NH2 | 564 |
| 99 | Cl | H | H | Cl | CF3 | H | H | H | H | CN | SCF3 | NH2 | 496 |
| 100 | Cl | H | H | Cl | NO2 | H | CF3 | H | H | CN | SCF3 | NH2 | 541 |
| 101 | Cl | H | H | Cl | Me | H | F | H | H | CN | SCF3 | NH2 | 460 |
| 102 | Cl | H | H | Cl | H | F | H | F | H | CN | SCF3 | NH2 | 464 |
| 103 | Cl | H | H | Cl | F | H | H | H | F | CN | SCF3 | NH2 | 464 |
| 104 | Cl | H | H | Cl | H | OCF3 | H | H | H | CN | SCF3 | NH2 | 512 |
| 105 | Cl | H | H | Cl | H | F | H | Cl | H | CN | SCF3 | NH2 | 480 |
| 106 | Cl | H | H | Cl | H | CN | H | H | H | CN | SCF3 | NH2 | 453 |
| 107 | Cl | H | H | Cl | H | OMe | H | H | H | CN | SCF3 | NH2 | 458 |
| 108 | Cl | H | H | Cl | H | H | CH2CN | H | H | CN | SCF3 | NH2 | 467 |
| 109 | Cl | H | H | Cl | H | H | Ms | H | H | CN | SCF3 | NH2 | 506 |
| 110 | Cl | H | H | Cl | H | H | SO2NH2 | H | H | CN | SCF3 | NH2 | 507 |
| 111 | Cl | H | H | Cl | H | H | NMe2 | H | H | CN | SCF3 | NH2 | 471 |
| 112 | Cl | H | H | Cl | OCH2O | | H | H | H | CN | SCF3 | NH2 | 472 |
| 113 | Cl | H | H | Cl | H | H | CN | H | H | CN | SCF3 | NH2 | 453 |
| 114 | Cl | H | H | Cl | H | H | CN | H | H | CN | SCF3 | NH2 | 453 |
| 115 | Cl | H | H | Cl | F | H | F | H | H | CN | SCF3 | NH2 | 464 |
| 116 | Cl | H | H | Cl | H | H | CONH2 | H | H | CN | SCF3 | NH2 | 471 |
| 117 | Cl | H | H | Cl | H | Cl | CN | H | H | CN | SCF3 | NH2 | 487 |
| 118 | Cl | H | H | Cl | H | CF3 | H | H | H | CN | SCF3 | NH2 | 496 |
| 119 | Cl | H | H | Cl | F | F | F | F | F | CN | SCF3 | NH2 | 518 |
| 120 | Cl | H | H | Cl | H | H | OPh | H | H | CN | SCF3 | NH2 | 520 |
| 121 | Cl | H | H | Cl | Cl | H | CF3 | H | H | CN | SCF3 | NH2 | 530 |
| 122 | Cl | H | H | Cl | H | OCF2O | | H | H | CN | SCF3 | NH2 | 508 |
| 123 | Cl | H | H | Cl | H | F | NH2 | H | H | CN | SCF3 | NH2 | 461 |
| 124 | Cl | H | H | Cl | H | CF3 | NO2 | H | H | CN | SCF3 | NH2 | 541 |
| 125 | Cl | H | H | Cl | OH | H | H | H | H | CN | SCF3 | NH2 | 444 |

TABLE 1-continued

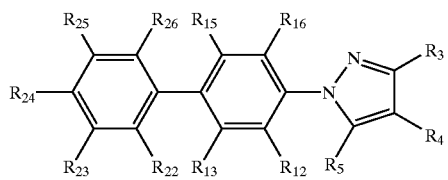

| CMP.NO | R12 | R13 | R15 | R16 | R22 | R23 | R24 | R25 | R26 | R3 | R4 | R5 | m/e |
|---|---|---|---|---|---|---|---|---|---|---|---|---|---|
| 126 | Cl | H | H | Cl | H | H | NH2 | H | H | CN | SCF3 | NH2 | 443 |
| 127 | Cl | H | H | Cl | H | H | OH | H | H | CN | SCF3 | NH2 | 444 |
| 128 | Cl | H | H | Cl | H | CF3 | H | NH2 | NH2 | CN | SCF3 | NH2 | 526 |
| 129 | Cl | H | H | Cl | H | F | Me | H | H | CN | SCF3 | NH2 | 460 |
| 130 | Cl | H | H | Cl | CN | F | H | H | H | CN | SCF3 | NH2 | 471 |
| 131 | Cl | H | H | Cl | H | Me | F | H | H | CN | SCF3 | NH2 | 460 |
| 132 | Cl | H | H | Cl | Me | H | H | F | H | CN | SCF3 | NH2 | 460 |
| 133 | Cl | H | H | Cl | Ph | H | H | H | H | CN | SCF3 | NH2 | 504 |
| 134 | Cl | H | H | Cl | OH | OMe | H | CHO | H | CN | SCF3 | NH2 | 502 |
| 135 | Cl | H | H | Cl | H | Cl | Cl | H | H | CN | S(O)2CH3 | NH2 | 474 |
| 136 | Cl | H | H | Cl | Cl | H | H | H | Cl | CN | S(O)2CH3 | NH2 | 474 |
| 137 | Cl | H | H | Cl | Cl | H | Cl | H | H | CN | S(O)2CH3 | NH2 | 474 |
| 138 | Cl | H | H | Cl | Cl | H | CF3 | H | Cl | CN | S(O)2CH3 | NH2 | 542 |
| 139 | Cl | H | H | Cl | H | H | OCF3 | H | H | CN | S(O)2CH3 | NH2 | 490 |
| 140 | Cl | H | H | Cl | CF3 | H | H | H | H | CN | S(O)2CH3 | NH2 | 474 |
| 141 | Cl | H | H | Cl | NO2 | H | CF3 | H | H | CN | S(O)2CH3 | NH2 | 519 |
| 142 | Cl | H | H | Cl | Me | H | F | H | H | CN | S(O)2CH3 | NH2 | 438 |
| 143 | Cl | H | H | Cl | H | F | H | F | H | CN | S(O)2CH3 | NH2 | 442 |
| 144 | Cl | H | H | Cl | F | H | H | H | F | CN | S(O)2CH3 | NH2 | 442 |
| 145 | Cl | H | H | Cl | F | H | H | H | H | CN | S(O)2CH3 | NH2 | 424 |
| 146 | Cl | H | H | Cl | H | H | CF3 | H | H | CN | C=NOH | NH2 | 439 |
| 147 | Cl | H | H | Cl | H | H | CF3 | H | H | CN | NO2 | NHAc | 483 |
| 148 | Cl | H | H | Cl | H | H | CF3 | H | H | CN | NO2 | NH2 | 441 |
| 149 | Cl | H | H | Cl | F | H | F | H | H | CN | S(O)2CH3 | NH2 | 442 |
| 150 | Cl | H | H | Cl | H | OCF3 | H | H | H | CN | S(O)2CH3 | NH2 | 490 |
| 151 | Cl | H | H | Cl | H | F | H | Cl | H | CN | S(O)2CH3 | NH2 | 458 |
| 152 | Cl | H | H | Cl | H | H | CONH2 | H | H | CN | S(O)2CH3 | NH2 | 449 |
| 153 | Cl | H | H | Cl | H | CN | H | H | H | CN | S(O)2CH3 | NH2 | 431 |
| 154 | Cl | H | H | Cl | H | H | SMe | H | H | CN | S(O)2CH3 | NH2 | 452 |
| 155 | Cl | H | H | Cl | H | OMe | H | H | H | CN | S(O)2CH3 | NH2 | 436 |
| 156 | Cl | H | H | Cl | H | H | CH2CN | H | H | CN | S(O)2CH3 | NH2 | 445 |
| 157 | Cl | H | H | Cl | H | H | Ms | H | H | CN | S(O)2CH3 | NH2 | 484 |
| 158 | Cl | H | H | Cl | H | H | SO2NH2 | H | H | CN | S(O)2CH3 | NH2 | 485 |
| 159 | Cl | H | H | Cl | H | H | NMe2 | H | H | CN | S(O)2CH3 | NH2 | 449 |
| 160 | Cl | H | H | Cl | OCH2O | | H | H | H | CN | S(O)2CH3 | NH2 | 450 |
| 161 | Cl | H | H | Cl | H | Cl | CN | H | H | CN | S(O)2CH3 | NH2 | 465 |
| 162 | Cl | H | H | Cl | H | H | CN | H | H | CN | S(O)2CH3 | NH2 | 431 |
| 163 | Cl | H | H | Cl | H | H | CO2Me | H | H | CN | S(O)2CH3 | NH2 | 464 |
| 164 | Cl | H | H | Cl | H | CF3 | H | H | H | CN | S(O)2CH3 | NH2 | 474 |
| 165 | Cl | H | H | Cl | F | F | F | F | F | CN | S(O)2CH3 | NH2 | 496 |
| 166 | Cl | H | H | Cl | H | H | OPh | H | H | CN | S(O)2CH3 | NH2 | 498 |
| 167 | Cl | H | H | Cl | Cl | H | CF3 | H | H | CN | S(O)2CH3 | NH2 | 508 |
| 168 | Cl | H | H | Cl | Cl | H | SF5 | H | Cl | CN | S(O)2CH3 | NH2 | 600 |
| 169 | Cl | H | H | Cl | Cl | H | OCF3 | H | Cl | CN | S(O)2CH3 | NH2 | 558 |
| 170 | Cl | H | H | Cl | H | OCF2O | | H | H | CN | S(O)2CH3 | NH2 | 486 |
| 171 | Cl | H | H | Cl | H | CO2H | OH | H | H | CN | S(O)2CH3 | NH2 | 466 |
| 172 | Cl | H | H | Cl | H | F | OH | H | H | CN | S(O)2CH3 | NH2 | 440 |
| 173 | Cl | H | H | Cl | H | F | NH2 | H | H | CN | S(O)2CH3 | NH2 | 439 |
| 174 | Cl | H | H | Cl | H | CF3 | NO2 | H | H | CN | S(O)2CH3 | NH2 | 519 |

TABLE 2

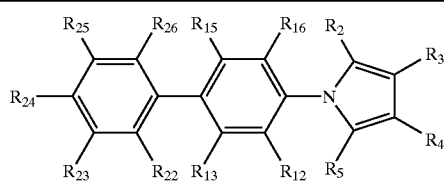

| CMP.NO | R12 | R13 | R15 | R16 | R2 | R22 | R23 | R24 | R25 | R26 | R3 | R4 | R5 | m/e |
|---|---|---|---|---|---|---|---|---|---|---|---|---|---|---|
| 175 | Cl | H | H | Cl | H | (CH=CH)2 | | H | H | H | SCFC12 | CN | Cl | 528 |
| 176 | Cl | H | H | Cl | Cl | H | (CH=CH)2 | | H | H | CN | SCFCl2 | H | 528 |

TABLE 2-continued

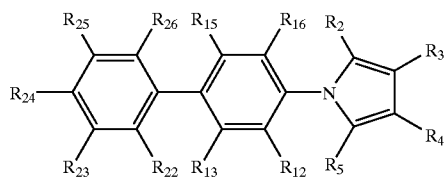

| CMP.NO | R12 | R13 | R15 | R16 | R2 | R22 | R23 | R24 | R25 | R26 | R3 | R4 | R5 | m/e |
|---|---|---|---|---|---|---|---|---|---|---|---|---|---|---|
| 177 | Cl | H | H | Cl | Cl | H | H | H | H | H | CN | SCFCl2 | H | 478 |
| 178 | Cl | H | H | Cl | H | H | H | Me | H | H | SCFCl2 | CN | Cl | 492 |
| 179 | Cl | H | H | Cl | H | Me | H | H | H | H | SCFCl2 | CN | Cl | 492 |
| 180 | Cl | H | H | Cl | Cl | H | NH2 | H | H | H | CN | SCFCl2 | H | 493 |
| 181 | Cl | H | H | Cl | H | H | NO2 | H | H | H | SCFCl2 | CN | Cl | 523 |
| 182 | Cl | H | H | Cl | Cl | H | NHAc | H | H | H | CN | SCFCl2 | H | 535 |
| 183 | Cl | H | H | Cl | H | CHO | H | H | H | H | SCFCl2 | CN | Cl | 506 |
| 184 | Cl | H | H | Cl | H | H | CHO | H | H | H | SCFCl2 | CN | Cl | 506 |
| 185 | Cl | H | H | Cl | Cl | H | H | CHO | H | H | CN | SCFCl2 | H | 506 |
| 186 | Cl | H | H | Cl | H | OMe | H | H | H | H | SCFCl2 | CN | Cl | 508 |
| 187 | Cl | H | H | Cl | H | H | OMe | H | H | H | SCFCl2 | CN | Cl | 508 |
| 188 | Cl | H | H | Cl | Cl | H | H | OMe | H | H | CN | SCFCl2 | H | 508 |
| 189 | Cl | H | H | Cl | H | H | H | SMe | H | H | CN | SCFCl2 | H | 524 |
| 190 | Cl | H | H | Cl | H | H | H | F | H | H | SCFCl2 | CN | Cl | 496 |
| 191 | Cl | H | H | Cl | Cl | H | F | H | H | H | CN | SCFCl2 | H | 496 |
| 192 | Cl | H | H | Cl | Cl | H | Cl | F | H | H | CN | SCFCl2 | H | 530 |
| 193 | Cl | H | H | Cl | H | H | H | Cl | H | H | SCFCl2 | CN | Cl | 512 |
| 194 | Cl | H | H | Cl | H | H | H | Br | H | H | SCFCl2 | CN | Cl | 556 |
| 195 | Cl | H | H | Cl | Cl | H | Cl | H | Cl | H | CN | SCFCl2 | H | 546 |
| 196 | Cl | H | H | Cl | H | Cl | H | Cl | H | H | SCFCl2 | CN | Cl | 546 |
| 197 | Cl | H | H | Cl | H | H | H | CF3 | H | H | SCFCl2 | CN | Cl | 546 |
| 198 | Cl | H | H | Cl | Cl | H | CF3 | H | H | H | CN | SCFCl2 | H | 546 |
| 199 | Cl | H | H | Cl | H | H | CF3 | H | CF3 | H | SCFCl2 | CN | Cl | 614 |
| 200 | Cl | H | H | Cl | Cl | H | Cl | H | H | H | CN | SCFCl2 | H | 512 |
| 201 | Cl | H | H | Cl | Cl | H | Br | H | H | H | CN | SCFCl2 | H | 556 |
| 202 | Cl | H | H | Cl | H | H | H | CF3 | H | H | S(O)CFCl2 | CN | Cl | 562 |
| 203 | Cl | H | H | Cl | H | H | H | CF3 | H | H | S(O)2CFCl2 | CN | Cl | 578 |
| 204 | H | H | H | H | H | H | H | CF3 | H | H | CHO | H | H | 315 |
| 205 | H | H | H | Me | H | H | H | CF3 | H | H | CHO | H | H | 329 |
| 206 | Me | H | H | Me | H | H | H | CF3 | H | H | CHO | H | H | 343 |
| 207 | Cl | H | H | H | H | H | H | CF3 | H | H | CHO | H | H | 349 |
| 208 | H | Cl | H | H | H | H | H | CF3 | H | H | CHO | H | H | 349 |
| 209 | Cl | H | H | Me | H | H | H | CF3 | H | H | CHO | H | H | 363 |
| 210 | Cl | H | H | Cl | H | H | H | CF3 | H | H | CHO | H | H | 383 |
| 211 | F | H | H | H | H | H | H | CF3 | H | H | CHO | H | H | 333 |
| 212 | F | H | H | F | H | H | H | CF3 | H | H | CHO | H | H | 351 |
| 213 | H | H | H | CF3 | H | H | H | CF3 | H | H | CHO | H | H | 383 |
| 214 | H | H | CF3 | H | H | H | H | CF3 | H | H | CHO | H | H | 383 |
| 215 | F | F | F | F | H | H | H | CF3 | H | H | CHO | H | H | 387 |
| 216 | Me | H | H | NO2 | H | H | H | CF3 | H | H | CHO | H | H | 374 |
| 217 | H | H | (CH=CH)2 | H | H | H | CF3 | H | H | CHO | H | H | 365 |

TABLE 3

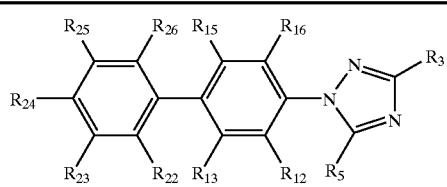

| CMP.NO | R12 | R13 | R15 | R16 | R22 | R23 | R24 | R25 | R26 | R3 | R5 | m/3 |
|---|---|---|---|---|---|---|---|---|---|---|---|---|
| 218 | Cl | H | H | Cl | H | H | CF3 | H | H | t-Bu | NH2 | 428 |
| 219 | Cl | H | H | Cl | H | H | CF3 | H | H | t-Bu | H | 413 |
| 220 | Cl | H | H | Cl | H | H | CF3 | H | H | t-Bu | Br | 491 |
| 221 | Cl | H | H | Cl | H | H | CF3 | H | H | CF3 | NH2 | 440 |
| 222 | Cl | H | H | Cl | H | NO2 | H | H | H | CF3 | NH2 | 417 |
| 223 | Cl | H | H | Cl | H | F | H | H | H | CF3 | NH2 | 390 |
| 224 | Cl | H | H | Cl | H | H | CF3 | H | H | CF3 | Br | 503 |
| 225 | Cl | H | H | Cl | H | H | CF3 | H | H | CF3 | H | 425 |
| 226 | Cl | H | H | Cl | H | (CH=CH)2 | H | H | CF3 | NH2 | 422 |
| 227 | Cl | H | H | Cl | (CH=CH)2 | H | H | H | CF3 | NH2 | 422 |

TABLE 3-continued

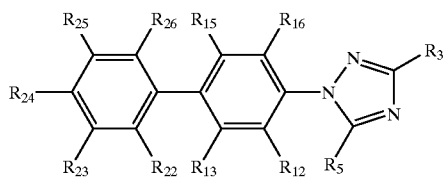

| CMP.NO | R12 | R13 | R15 | R16 | R22 | R23 | R24 | R25 | R26 | R3 | R5 | m/3 |
|---|---|---|---|---|---|---|---|---|---|---|---|---|
| 228 | Cl | H | H | Cl | Me | H | H | H | H | CF3 | NH2 | 386 |
| 229 | Cl | H | H | Cl | H | OMe | H | H | H | CF3 | NH2 | 402 |
| 230 | Cl | H | H | Cl | H | H | OMe | H | H | CF3 | NH2 | 402 |
| 231 | Cl | H | H | Cl | H | H | SMe | H | H | CF3 | NH2 | 418 |
| 232 | Cl | H | H | Cl | H | H | F | H | H | CF3 | NH2 | 390 |
| 233 | Cl | H | H | Cl | H | H | Cl | H | H | CF3 | NH2 | 406 |
| 234 | Cl | H | H | Cl | H | H | Br | H | H | CF3 | NH2 | 450 |
| 235 | Cl | H | H | Cl | H | Cl | H | Cl | H | CF3 | NH2 | 440 |
| 236 | Cl | H | H | Cl | Cl | H | Cl | H | H | CF3 | NH2 | 440 |
| 237 | Cl | H | H | Cl | H | CF3 | H | H | H | CF3 | NH2 | 440 |
| 238 | Cl | H | H | Cl | H | Cl | H | H | H | CF3 | NH2 | 406 |
| 239 | Cl | H | H | Cl | H | Br | H | H | H | CF3 | NH2 | 450 |
| 240 | Cl | H | H | Cl | (CH=CH)2 | | H | H | H | CF3 | H | 407 |
| 241 | Cl | H | H | Cl | H | H | H | H | H | CF3 | H | 357 |
| 242 | Cl | H | H | Cl | H | H | Me | H | H | CF3 | H | 371 |
| 243 | Cl | H | H | Cl | H | NO2 | H | H | H | CF3 | H | 402 |
| 244 | Cl | H | H | Cl | H | CHO | H | H | H | CF3 | H | 385 |
| 245 | Cl | H | H | Cl | H | OMe | H | H | H | CF3 | H | 387 |
| 246 | Cl | H | H | Cl | H | H | F | H | H | CF3 | H | 375 |
| 247 | Cl | H | H | Cl | H | H | F | H | H | CF3 | H | 375 |
| 248 | Cl | H | H | Cl | H | F | H | H | H | CF3 | H | 375 |
| 249 | Cl | H | H | Cl | H | Cl | F | H | H | CF3 | H | 409 |
| 250 | Cl | H | H | Cl | H | (CH=CH)2 | | H | H | CF3 | H | 407 |
| 251 | Cl | H | H | Cl | H | NHAc | H | H | H | CF3 | H | 414 |
| 252 | Cl | H | H | Cl | CHO | H | H | H | H | CF3 | H | 385 |
| 253 | Cl | H | H | Cl | H | H | CHO | H | H | CF3 | H | 385 |
| 254 | Cl | H | H | Cl | OMe | H | H | H | H | CF3 | H | 387 |
| 255 | Cl | H | H | Cl | H | H | CF3 | H | H | SMe | H | 403 |
| 256 | Cl | H | H | Cl | H | H | CF3 | H | H | SMe | NH2 | 418 |
| 257 | Cl | H | H | Cl | H | H | CF3 | H | H | SOMe | NH2 | 434 |
| 258 | Cl | H | H | Cl | H | H | CF3 | H | H | SOMe | H | 419 |
| 259 | Cl | H | H | Cl | H | H | CF3 | H | H | SOMe | Br | 497 |
| 260 | Cl | H | H | Cl | H | H | CF3 | H | H | SCCl2F | H | 489 |
| 261 | Cl | H | H | Cl | H | H | CF3 | H | H | S(O)CCl2F | H | 505 |
| 263 | Cl | H | H | Cl | H | H | CF3 | H | H | S(O)2CCl2F | H | 521 |

TABLE 4

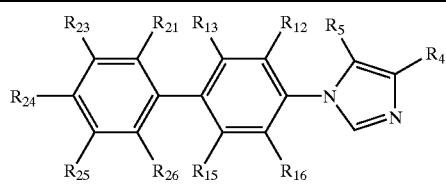

| CMP.NO | R12 | R13 | R15 | R16 | R21 | R23 | R24 | R25 | R26 | R4 | R5 | m/e |
|---|---|---|---|---|---|---|---|---|---|---|---|---|
| 264 | Cl | H | H | Cl | H | H | CF3 | H | H | SCCl2F | H | 488 |
| 265 | Cl | H | H | Cl | H | H | CF3 | H | H | SCCl2F | Br | 566 |
| 266 | Cl | H | H | Cl | H | H | CF3 | H | H | SCCl2F | NH2 | 503 |
| 267 | Cl | H | H | Cl | H | H | CF3 | H | H | SO2CCl2F | Br | 537 |
| 268 | Cl | H | H | Cl | H | H | CF3 | H | H | SOCCl2F | H | 504 |
| 269 | Cl | H | H | Cl | H | H | CF3 | H | H | SO2CCl2F | H | 520 |
| 270 | H | H | H | F | H | H | CF3 | H | H | SOCCl2F | H | 454 |
| 271 | Cl | H | H | Cl | Cl | H | CF3 | H | Cl | SOCCl2F | H | 572 |
| 272 | Cl | H | H | Cl | H | H | OCF3 | H | H | SOCCl2F | H | 520 |
| 273 | Cl | H | H | Cl | H | OCF2O | | H | H | SOCCl2F | H | 516 |
| 274 | Cl | H | H | Cl | H | H | H | H | H | SOCCl2F | H | 436 |
| 275 | Cl | H | H | Cl | Me | H | Me | Me | H | SOCCl2F | H | 478 |
| 276 | Cl | H | H | Cl | Me | H | H | H | Me | SOCCl2F | H | 464 |
| 277 | Cl | H | H | Cl | H | H | t-Bu | H | H | SOCCl2F | H | 492 |
| 278 | Cl | H | H | Cl | H | CF3 | H | CF3 | H | SOCCl2F | H | 572 |
| 279 | Cl | H | H | Cl | H | CH2CN | H | H | H | SOCCl2F | H | 475 |

TABLE 4-continued

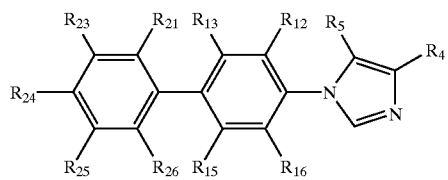

| CMP.NO | R12 | R13 | R15 | R16 | R21 | R23 | R24 | R25 | R26 | R4 | R5 | m/e |
|---|---|---|---|---|---|---|---|---|---|---|---|---|
| 280 | Cl | H | H | Cl | H | | OCH2O | H | H | SOCCl2F | H | 480 |
| 281 | Cl | H | H | Cl | H | F | H | F | H | SOCCl2F | H | 472 |
| 282 | Cl | H | H | Cl | F | F | NH2 | F | F | SOCCl2F | H | 523 |
| 283 | Cl | H | H | Cl | NO2 | H | CF3 | H | H | SOCCl2F | H | 549 |
| 284 | Cl | H | H | Cl | H | H | CH2CN | H | H | SOCCl2F | H | 475 |
| 285 | Cl | H | H | Cl | H | H | n-Bu | H | H | SOCCl2F | H | 492 |
| 286 | Cl | H | H | Cl | Cl | H | Cl | H | H | SOCCl2F | H | 504 |
| 287 | Cl | H | H | Cl | H | NO2 | NH2 | Me | Me | SOCCl2F | H | 524 |
| 288 | Cl | H | H | Cl | Cl | H | CF3 | H | H | SOCCl2F | H | 538 |
| 289 | Cl | H | H | Cl | Cl | H | Cl | H | Cl | SOCCl2F | H | 538 |
| 290 | Cl | H | H | Cl | F | F | CF3 | F | F | SOCCl2F | H | 576 |
| 291 | Cl | H | H | Cl | F | F | CN | F | F | SOCCl2F | H | 533 |
| 292 | Cl | H | H | Cl | 5-tetrazolyl | H | H | H | H | SOCCl2F | H | 504 |
| 293 | Cl | H | H | Cl | H | H | CN | H | H | SOCCl2F | H | 461 |
| 294 | Cl | H | H | Cl | Cl | H | SF5 | H | Cl | SOCCl2F | H | 630 |
| 295 | H | H | H | F | H | H | CF3 | H | H | SOCCl2F | H | 438 |
| 296 | Cl | H | H | Cl | H | H | CF3 | H | H | SCF3 | H | 456 |
| 297 | Cl | H | H | Cl | H | H | CF3 | H | H | SOCF3 | H | 472 |
| 298 | Cl | H | H | Cl | H | H | CF3 | H | H | SO₂CF3 | H | 488 |

The present invention provides also a method for controlling pests at a locus comprising applying to said locus a pesticidally effective amount of a compound of formula (I), or a pesticidal composition comprising a pesticidally effective amount of a compound of formula (I) and a pesticidally acceptable carrier therefor. In a preferred embodiment, the invention provides a method for controlling insects at a locus comprising applying to said locus an insecticidally effective amount of a compound of formula (I), or an insecticidally effective amount of an insecticidal composition comprising an insecticidally effective amount of a compound of formula (I) and an agriculturally acceptable inert carrier therefor. Preferably, the locus to which the pesticidally (especially insecticidally) effective amount is applied is a crop-growing area, that is, an area in which a crop is growing or in which a crop has been planted, or an area in which a crop will be planted/grown.

The compositions which can be used in the invention for the pesticidal/insecticidal treatment of the invention can comprise from about 0.001 to 95% of the compound of formula (I).

The diluted liquid formulations, as applied to the locus to be treated or crop, generally comprise from about 0.001 to about 3% of active ingredient of formula (I), preferably from about 0.1 to about 0.5%.

The solid formulations as applied to the locus or crop generally comprise from about 0.1 to about 8% of active ingredient of formula (I), preferably from about 0.5 to about 1.5%.

The concentrated compositions are the compositions which are commercialized or transported or stored. For application to plants, they are normally diluted in water and applied in such diluted form. The diluted forms are part of the invention as well as the concentrated forms.

The concentrated formulations generally comprise from about 5 to about 95% of active ingredient of formula (I), preferably from about 10 to about 50%.

The insecticidal compositions of the invention can be applied once, or more than once, throughout the whole insect season. Insecticidal compositions according to the invention are usually applied to the locus to be treated or crop area at a rate of from about 0.01 to about 2 kg/ha of active ingredient, preferably from about 0.1 to about 1 kg/ha.

The concentrated insecticidal compositions according to the invention can be in the form of a solid, e.g., dusts or granules or wettable powders, or, preferably, in the form of a liquid, such as an emulsifiable concentrate or a true solution.

The compositions according to the instant invention generally comprise from about 0.5 to about 95% of active ingredient of formula (I). The remainder of the composition up to 100% comprises a carrier as well as various additives such as those hereafter indicated.

By "carrier", there is meant herein an organic or inorganic material, which can be natural or synthetic, and which is associated with the active ingredient and which facilitates its application to the locus to be treated or crop. This carrier is thus generally inert and should be agriculturally acceptable, especially on the contemplated or treated locus or crop. The carrier can be solid (clay, silicates, silica, resins, wax, fertilizers, etc.) or liquid (water, alcohols, ketones, oil solvents, saturated or unsaturated hydrocarbons, chlorinated hydrocarbons, liquified petroleum gas, etc.).

Among the many additives, the compositions of the invention can comprise surfactants as well as other ingredients such as dispersants, stickers, antifoam agents, antifreezing agents, dyestuffs, thickeners, adhesives, protective colloids, penetrating agents, stabilizing agents, sequestering agents, antiflocculating agents, corrosion inhibitors, pigments and polymers.

More generally, the compositions of the invention can comprise all kinds of solid or liquid additives which are known in the art of insecticides and insecticidal treatments.

The surfactants can be of the emulsifying or wetting type, ionic or non-ionic. Possible surfactants are salts of polyacrylic or lignosulfonic acids; salts of phenolsulfonic or naphthalenesulfonic acids; polycondensates of ethylene oxide with fatty alcohols or fatty acids or fatty amines or substituted phenols (particularly alkylphenols or arylphenols); ester-salts of sulfosuccinic acids; taurine derivatives, such as alkyl taurates; phosphoric esters; or esters of alcohols or polyoxyethylated phenols. When the spraying vehicle is water, the use of at least one surfactant is generally required because the active ingredients are not water-soluble.

The method of application of the compositions of the invention is generally the spraying of a mixture which has been previously made, by dilution of more concentrated formulations according to the invention.

Solid compositions can be powders for dusting or for dispersion (wherein the content of active ingredient can be up to 100%) and granules, especially extruded or compacted granules, or granules which have been made by impregnation of a powder (the content of active ingredient in such powders being between about 1 and about 80%).

Liquid compositions or compositions which have to be liquid when applied include solutions, water-soluble concentrates, emulsifiable concentrates, emulsions, wettable powders or pastes or water-dispersible granules.

Emulsifiable concentrates generally comprise from about 10 to about 80% of active ingredient; the emulsions when applied generally comprise from about 0.01 to about 20% of active ingredient.

For example, the emulsifiable concentrates can comprise the solvent and, to the extent needed, from about 2 to about 20% of suitable additives such as stabilizers, surfactants, penetrating agents, corrosion inhibitors or other additives already recited.

These concentrates are usually diluted in tank water so as to obtain the dilution appropriate for spraying.

The concentrated suspensions can also be applied by spraying and have to be fluid without allowing any solid to separate and fall to the bottom. Generally they comprise from about 1 to about 75% of active ingredient (preferably from about 2 to about 50%), from about 0.5 to about 15% of surfactant, from about 0.1 to about 10% of thickener, from 0 to about 10% of other suitable additives as already indicated, the remainder being water or an organic liquid wherein the active ingredient is insoluble or has a low solubility.

The wettable powders generally comprise the active ingredient (from about 1 to about 95%, preferably from about 2 to about 80%), the solid carrier, a wetting agent (from 0 to about 5%), a dispersing agent (from about 3 to about 10%) and, to the extent needed, from 0 to about 10% of other additives such as stabilizers and others as already listed.

In order to obtain these wettable powders or dusting powders, it is appropriate to intimately mix the active ingredients and the additives, as by grinding in a mill or similar device.

Dispersible granules are generally made by agglomeration of a powder, followed by an appropriate granulation process.

The emulsions herein described can be of the oil-in-water or water-in-oil types. Fluidity of the emulsions can range from low viscosities up to high viscosities approaching those of gels.

Among these many compositions or formulations, one skilled in the art can choose the one most appropriate, according to the specific conditions of the treatment problem.

The compounds and compositions of the invention can also be used in admixtures with another pesticide, e.g., an insecticide, acaricide or herbicide.

The compounds of the invention may also be used in controlling pests found in non-agricultural domains.

In the field of veterinary medicine or livestock husbandry or in the maintenance of public health against arthropods, helminths or protozoa which are parasitic internally or externally upon vertebrates, particularly warm-blooded vertebrates, for example man or domestic animals, e.g. cattle, sheep, goats, equines, swine, poultry, dogs or cats, for example Acarina, including ticks (e.g. Ixodes spp., Boolphilus spp. e.g. *Boophilus microplus*, Amblyomma spp., Hyalomma spp., Rhipicephalus spp. e.g. *Rhipiceghalus appendiculatus*, Haemaphysalis spp., Dermacentor spp., Ornithodorus spp. (e.g. *Ornithodorus moubata*) and mites (e.g. Damalinia spp., *Dermahyssus gallinae*, Sarcoptes spp. e.g. *Sarcoptes scabiei*, Psoroptes spp., Chorioptes spp;, Demodex spp., Eutrombicula spp.,); Diptera (e.g. Aedes spp., Anopheles spp., Dermatobia spp., Haematobia spp., Musca spp., Hippoboscidae spp., Hypoderma spp., Gasterophilus spp., Simulium spp); Stomoxys spp., Hemiptera (e.g. Triatoma spp); Phthirapter (e.g. Damalinia spp., Linognathus spp.); Siphonaptera (e.g. Ctenocephalides spp.); Dictyootera (e.g. Periplaneta spp., Blatella spp.); Hymenoptera (e.g. *Monomorium pharaonis*); for example against infections of the gastro-intestinal tract caused by parasitic nematode worms, for example members of the family Trichostrongylidae, *Nippostrongylus brasiliensis, Trichinella spiralis, Haemonchus contortus, Trichostrongylus colubriformis, Nematodirus batus, Ostertagis circumcincta, Trichostrongylus axei*, Cooperia spp. and *Hymenolepis nana*; in the control and treatment of protozoal diseases caused by, for example, Eimeria spp. e.g. *Eimeria tenella, Eimeria acervulina, Eimeria brunetti, Eimeria maxima* and *Eimeria necatrix, Trypanosoms cruzi*, Leishaminia spp., Plasmodium spp., Babesis spp., Trichomonadidae spp., Histomanas spp., Giardia spp., Toxoplasma spp., *Entamoeba histolytica* and Theileria spp.

Furthermore the compounds of the invention may be useful for coccidiosis, a disease caused by infections from protozoan parasites of the genus Eimeria.

Compositions

Solid or liquid compositions for application topically to animals, timber, stored products or household goods usually contain from about 0.00005% to about 90%, more particularly from about 0.001% to about 10%, by weight of one or more compounds of general formula (I). For administration to animals orally or parenterally, including percutaneously solid or liquid compositions, these normally contain from about 0.1% to about 90% by weight of one or more compounds of general formula (I). Medicated feedstuffs normally contain from about 0.001% to about 3% by weight of one or more compounds of general formula (I). Concentrates or supplements for mixing with feedstuffs normally contain from about 5% to about 90%, preferably from about 5% to about 50%, by weight of one or more compounds of general formula(I). Mineral salt licks normally contain from about 0.1% to about 10% by weight of one or more compounds of general formula (I).

Dusts or liquid compositions for application to livestock, persons, goods, premises or outdoor areas may contain from about 0.0001% to about 15%, more especially from about 0.005% to about 2.0%, by weight, of one or more compounds of general formula (I). Suitable concentrations in treated waters are between about 0.0001 ppm and about 20 ppm, more particularly about 0.001 ppm to about 5.0 ppm of one or more compounds of general formula (I) and may be used therapeutically in fish farming with appropriate exposure times. Edible baits may contain from about 0.01% to about 5%, preferably from about 0.01% to about 1.0%, by weight, of one or more compounds of general formula (I).

When administered to vertebrates parenterally, orally or by percutaneous or other means, the dosage of compounds of general formula (I) will depend upon the species, age, or health of the vertebrate and upon the nature and degree of its actual or potential infestation by arthropod, hehminth or protozoan pests. A single dose of about 0.1 to about 100 mg, preferably about 2.0 to about 20.0 mg, per kg body weight of the animal or doses of about 0.01 to about 20.0 mg, preferably about 0.1 to about 5.0 mg, per kg body weight of the animal per day, for sustained medication, are generally suitable by oral or parenteral administration. By use of sustained release formulations or devices, the daily doses required over a period of months may be combined and administered to animals on a single occasion.

The following methods were used to apply the compounds of the invention and to observe the results obtained therewith: a foliar/contact spray on sucking (aphids) or chewing (Lepidoptera) insects.

The species tested were as follows:

| GENUS, SPECIES | COMMON NAME |
| --- | --- |
| Aphis gossypii | cotton leaf aphid |
| Musca domestica | housefly |
| Diabrotica virgifera | Western cornrootworm |
| Periplaneta americana | American Cockroaches |
| Spodoptera eridania | Southern armyworm |

The Housefly Bait/Contact Test

About 25 four to six-day-old adult houseflies were anesthetized and placed in a cage with a sugar water bait solution containing the compound. The concentration of the selected compound of formula (I) in the bait solution was 50 ppm. After 24 hours, flies which showed no movement on stimulation were considered dead.

Foliar Application (Contact Test) With Aphids

Aphid-infested cotton plants were placed on a revolving turntable, and sprayed to runoff with a 100 ppm formulation of the selected compound of formula (I). The treated, *A. gossypii*-infested plants were held for three days after treatment, after which the dead aphids were counted.

Application on Western Cornrootworm

Jars are filled with 60 g dry soil homogeneously mixed with 5 ml aqueous solution containing the compound to be tested. After drying, four germinated corn seedlings are placed in the bottom of each jar and the soil is wetted. Then ten newly born larvae are placed in each jar. The jars are stored for six days at 27° C. under 70% of relative humidity. The number of surviving larvae are then counted.

Application by Contact to Cockroaches

The inner wall of a 100 ml jar is covered by shaking 2 ml of pesticidal formulation. Furthermore, a pellet of dog chow is placed into a jar and the pesticidal formulation is absorbed on the pellet, using excess liquid. The jar is then left open up to evaporation of liquid. Cockroach nymphs are placed in the jar and mortality is assessed after five days.

Application to Southern Armyworm

Leaves of soybeans were sprayed to run-off with a spray of various concentrations. Then the leaves were allowed to dry, excised, and placed into a container with five larvae. The containers are stored for five days at 25° C. under 50% relative humidity. Mortality ratings are then counted.

Application to Caenorhabditis Elegans (Nematode Worm)

This test is significative for animal health applications of active ingredient.

Test formulation are prepared by mixing 2 microliters of dimethylsulfoxide with 100 microliters of a solution of *Escherichia Coli* (which is food for *C. elegans*). 98 microliters of this mixture are then mixed with an inoculum solution which consists of mixed life stages of *C. Elegans* (about 50 worms). This new mixture is stored 7 days at 20° C. Mortality is then visually assessed as well as the behavior of the worm. For the mortality, the rating is either 1 (large increase in number of the population, similar to the control which is trebbling in 7 days) or 3 (slight increase of the population, but significantly less increase than the control) or 5 (little to no increase in the population). For the behavior effect, the rating is either 1 (normal motion) or 3 (motion is slower than the control) or 5 (little to no movement).

All the hereinabove prepared compounds show a positive activity in one or more of these tests (rather good activity on *C. elegans*).

While the invention has been described in terms of various preferred embodiments, the person skilled in the art will appreciate that various modifications, substitutions, omissions and changes can be made without departing from the spirit thereof. Accordingly, it is intended that the scope of the present invention be limited solely by the scope of the following claims, including equivalents thereof.

What is claimed is:

1. A compound of formula (I):

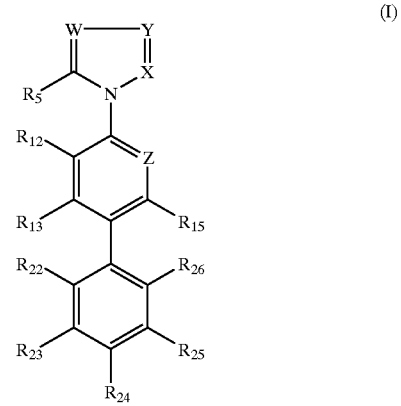

wherein:
X is N;
Y is C—$R_3$;
W is N;
$R_3$ is halogen, hydroxy, alkyl, cycloalkyl, haloalkyl, alkoxy, haloalkoxy, CN, $NO_2$, —$S(O)_nR_8$, alkylcarbonyl, alkoxycarbonyl, aminocarbonyl, alkylaminocarbonyl, dialkylaminocarbonyl, hydroxycarbonyl, aminosulfonyl, alkylaminosulfonyl, or dialkylaminosulfonyl;
$R_5$ is hydrogen, halogen, —$NR_9R_{10}$, —$N=CR_{11}R_{19}$, —$S(O)_nR_8$, formyl, alkylcarbonyl, haloalkylcarbonyl, cyano, alkyl, haloalkyl, hydrazino, alkoxycarbonyl, alkylthiocarbonyl, 1H-pyrrol-1-yl or 1H-pyrazol-1-yl;
$R_8$ is alkyl, haloalkyl, alkenyl, or alkynyl, or $R_8$ is a cycloalkyl ring having 3 to 5 carbon atoms
$R_{11}$ is H or alkyl;
$R_{19}$ is hydrogen, alkyl, haloalkyl, alkoxy, haloalkoxy, alkylthio, amino, monoalkylamino, or dialkylamino; or $R_{19}$ is phenyl, thienyl, pyridyl or furyl, each of which is unsubstituted or substituted with one or more substituents selected from the group consisting of alkyl, haloalkyl, halogen, $NO_2$, CN, alkoxy, haloalkoxy, OH, alkylcarbonyl and alkylcarbonyloxy;

$R_9$ and $R_{10}$, independently of each other, are H, alkyl, haloalkyl, alkylcarbonyl, haloalkylcarbonyl, $R_8S(O)_n$, formyl, alkenyl, alkynyl, alkoxycarbonyl, alkylthiocarbonyl, or aroyl; or $R_9$ and $R_{10}$ are joined so as to together form a divalent radical having 4 to 6 atoms in the chain, said divalent radical being alkylene, alkyleneoxyalkylene or alkyleneaminoalkylene, the alkyl portions of $R_9$ and $R_{10}$ being optionally substituted by $R_7$;

$R_7$ is cyano, nitro, alkoxy, haloalkoxy, $R_8S(O)_n$, —C(O)alkyl, alkoxycarbonyl, aminocarbonyl, alkylaminocarbonyl, dialkylaminocarbonyl, —$CO_2H$, halogen, hydroxy, aminosulfonyl, alkylaminosulfonyl or dialkylaminosulfonyl;

Z is N or C—$R_{16}$, n is zero, one or two;

$R_{12}$, $R_{13}$, $R_{15}$ and $R_{16}$, independently of one another, are hydrogen, halogen, alkyl, haloalkyl, cyanoalkyl, cyano, nitro, amino, hydrazino, alkoxy, haloalkoxy, alkylsulfenyl, alkylsulfinyl, alkylsulfonyl, haloalkylsulfenyl, haloalkylsulfinyl, haloalkylsulfonyl, formyl, alkylcarbonyl or alkoxycarbonyl;

$R_{22}$, $R_{23}$, $R_{24}$, $R_{25}$, and $R_{26}$, independently of one another, are hydrogen, halogen, alkyl, haloalkyl, cyanoalkyl, cyano, nitro, amino, hydrazino, alkoxy, haloalkoxy, haloalkylcarbonyl, formyl, alkylcarbonyl, thioamide, amide, alkoxycarbonyl, $SF_5$, or $R_8S(O)_n$; or $R_{22}$ and $R_{23}$ or $R_{23}$ and $R_{24}$ or $R_{25}$ and $R_{26}$ together form divinylidene (CH═CH—CH═CH—), methylenedioxy (—O—$CH_2$—O—) or difluoromethylenedioxy (—O—$CF_2$—O—) so as to form a cyclic ring vicinal to the phenyl ring;

or a pesticidally acceptable salt thereof.

2. A compound according to claim 1, wherein $R_9$ and $R_{10}$ are joined together to form with the adjacent nitrogen atom a morpholine, pyrrolidine, piperidine or piperazine ring, optionally substituted by $R_7$.

3. A compound according to claim 1, wherein $R_{24}$ is halogen, haloalkyl or haloalkoxy.

4. A compound according to claim 1, wherein $R_5$ is —$NR_9R_{10}$.

5. A compound according to claim 4, wherein $R_5$ is —$NH_2$.

6. A compound according to claim 1, wherein $R_8$ is lower alkyl or haloalkyl.

7. A compound according to claim 1, having at least one feature selected from the group consisting of:

$R_3$ is CN or halogen;

$R_5$ is hydrogen, halogen, $C_1$–$C_3$ alkyl, $C_1$–$C_3$ haloalkyl, or —$NR_9R_{10}$;

$R_8$ is methyl, ethyl, —$CF_3$, —$CFCl_2$, or —$CF_2Cl$;

$R_{12}$ and $R_{16}$, independently of each other, are F, Cl, Br or H;

$R_{13}$ and $R_{15}$ are H;

$R_{24}$ is —$CF_3$, —$OCF_3$, —$CHF_2$, —$S(O)_nCF_3$, —$CFCl_2$, —$CF_2Cl$, —$OCF_2Cl$, —$OCFCl_2$, Cl, Br or F; and Z is CCl, CF, CBr or N.

8. A compound according to claim 1, wherein the $S(O)_nR_8$ substituent of formula (I) is: methylthio, methylsulfinyl, methylsulfonyl, ethylsulfinyl, ethylsulfonyl, ethylthio, cyclopropylsulfinyl, cyclopropylthio, cyclopropylsulfonyl, isopropylsulfinyl, isopropylsulfonyl, isopropylthio, trifluoromethylthio, trifluoromethylsulfinyl, trifluoromethylsulfonyl, dichlorofluoromethylthio, dichlorofluoromethylsulfenyl, dichlorofluoromethylsulfonyl, chlorodifluoromethylthio, chlorodifluoromethylsulfonyl or chlorodifluoromethylsulfinyl.

9. A compound according to claim 7, wherein the $S(O)_nR_8$ substituent of formula (I) is: trifluoromethylthio, trifluoromethylsulfinyl, trifluoromethylsulfonyl, dichlorofluoromethylthio, dichlorofluoromethylsulfinyl, dichlorofluoromethylsulfonyl, chlorodifluoromethylthio, chlorodifluoromethylsulfonyl or chlorodifluoromethylsulfinyl.

10. The compound according to claim 1, having formula (I) wherein $R_3$ is $CF_3$; $R_5$ is $NH_2$; Z is C—$R_{16}$; $R_{12}$ is Cl; $R_{13}$ is H; $R_{15}$ is H; $R_{16}$ is Cl; $R_{22}$ is H; $R_{23}$ is H; $R_{24}$ is Br; $R_{25}$ is H; and $R_{26}$ is H.

11. The compound according to claim 1, having the formula (I) wherein:

(a) $R_3$ is t-butyl; $R_5$ is $NH_2$; Z is C—$R_{16}$; $R_{12}$ is Cl; $R_{13}$ is H; $R_{15}$ is H; $R_{16}$ is Cl; $R_{22}$ is H; $R_{23}$ is H; $R_{24}$ is $CF_3$; $R_{25}$ is H; and $R_{26}$ is H;

(b) $R_3$ is t-butyl; $R_5$ is H; Z is C—$R_{16}$; $R_{12}$ is Cl; $R_{13}$ is H; $R_{15}$ is H; $R_{16}$ is Cl; $R_{22}$ is H; $R_{23}$ is H; $R_{24}$ is $CF_3$; $R_{25}$ is H; and $R_{26}$ is H;

(c) $R_3$ is t-butyl; $R_5$ is Br; Z is C—$R_{16}$; $R_{12}$ is Cl; $R_{13}$ is H; $R_{15}$ is H; $R_{16}$ is Cl; $R_{22}$ is H; $R_{23}$ is H; $R_{24}$ is $CF_3$; $R_{25}$ is H; and $R_{26}$ is H;

(d) $R_3$ is $CF_3$; $R_5$ is $NH_2$; Z is C—$R_{16}$; $R_{12}$ is Cl; $R_{13}$ is H; $R_{15}$ is H; $R_{16}$ is Cl; $R_{22}$ is H; $R_{23}$ is H; $R_{24}$ is $CF_3$; $R_{25}$ is H; and $R_{26}$ is H;

(e) $R_3$ is $CF_3$; $R_5$ is $NH_2$; Z is C—$R_{16}$; $R_{12}$ is Cl; $R_{13}$ is H; $R_{15}$ is H; $R_{16}$ is Cl; $R_{22}$ is H; $R_{23}$ is $NO_2$; $R_{24}$ is H; $R_{25}$ is H; and $R_{26}$ is H;

(f) $R_3$ is $CF_3$; $R_5$ is $NH_2$; Z is C—$R_{16}$; $R_{12}$ is Cl; $R_{13}$ is H; $R_{15}$ is H; $R_{16}$ is Cl; $R_{22}$ is H; $R_{23}$ is F; $R_{24}$ is H; $R_{25}$ is H; and $R_{26}$ is H;

(g) $R_3$ is $CF_3$; $R_5$ is Br; Z is C—$R_{16}$; $R_{12}$ is Cl; $R_{13}$ is H; $R_{15}$ is H; $R_{16}$ is Cl; $R_{22}$ is H; $R_{23}$ is H; $R_{24}$ is $CF_3$; $R_{25}$ is H; and $R_{26}$ is H;

(h) $R_3$ is $CF_3$; $R_5$ is H; Z is C—$R_{16}$; $R_{12}$ is Cl; $R_{13}$ is H; $R_{15}$ is H; $R_{16}$ is Cl; $R_{22}$ is H; $R_{23}$ is H; $R_{24}$ is $CF_3$; $R_{25}$ is H; and $R_{26}$ is H;

(i) $R_3$ is $CF_3$; $R_5$ is $NH_2$; Z is C—$R_{16}$; $R_{12}$ is Cl; $R_{13}$ is H; $R_{15}$ is H; $R_{16}$ is Cl; $R_{22}$ is H; $R_{23}$ and $R_{24}$ together are (CH═CH)$_2$; $R_{25}$ is H; and $R_{26}$ is H;

(j) $R_3$ is $CF_3$; $R_5$ is $NH_2$; Z is C—$R_{16}$; $R_{12}$ is Cl; $R_{13}$ is H; $R_{15}$ is H; $R_{16}$ is Cl; $R_{22}$ and $R_{23}$ together are (CH═CH)$_2$; $R_{24}$ is H; $R_{25}$ is H; and $R_{26}$ is H;

(k) $R_3$ is $CF_3$; $R_5$ is $NH_2$; Z is C—$R_{16}$; $R_{12}$ is Cl; $R_{13}$ is H; $R_{15}$ is H; $R_{16}$ is Cl; $R_{22}$ is $CH_3$; $R_{23}$ is H; $R_{24}$ is H; $R_{25}$ is H; and $R_{26}$ is H;

(l) $R_3$ is $CF_3$; $R_5$ is $NH_2$; Z is C—$R_{16}$; $R_{12}$ is Cl; $R_{13}$ is H; $R_{15}$ is H; $R_{16}$ is Cl; $R_{22}$ is H; $R_{23}$ is $OCH_3$; $R_{24}$ is H; $R_{25}$ is H; and $R_{26}$ is H;

(m) $R_3$ is $CF_3$; $R_5$ is $NH_2$; Z is C—$R_{16}$; $R_{12}$ is Cl; $R_{13}$ is H; $R_{15}$ is H; $R_{16}$ is Cl; $R_{22}$ is H; $R_{23}$ is H; $R_{24}$ is $OCH_3$; $R_{25}$ is H; and $R_{26}$ is H;

(n) $R_3$ is $CF_3$; $R_5$ is $NH_2$; Z is C—$R_{16}$; $R_{12}$ is Cl; $R_{13}$ is H; $R_{15}$ is H; $R_{16}$ is Cl; $R_{22}$ is H; $R_{23}$ is H; $R_{24}$ is $SCH_3$; $R_{25}$ is H; and $R_{26}$ is H;

(o) $R_3$ is $CF_3$; $R_5$ is $NH_2$; Z is C—$R_{16}$; $R_{12}$ is Cl; $R_{13}$ is H; $R_{15}$ is H; $R_{16}$ is Cl; $R_{22}$ is H; $R_{23}$ is F; $R_{24}$ is H; $R_{25}$ is H; and $R_{26}$ is H;

(p) $R_3$ is $CF_3$; $R_5$ is $NH_2$; Z is $C-R_{16}$; $R_{12}$ is Cl; $R_{13}$ is H; $R_{15}$ is H; $R_{16}$ is Cl; $R_{22}$ is H; $R_{23}$ is H; $R_{24}$ is Cl; $R_{25}$ is H; and $R_{26}$ is H;

(q) $R_3$ is $CF_3$; $R_5$ is $NH_2$; Z is $C-R_{16}$; $R_{12}$ is Cl; $R_{13}$ is H; $R_{15}$ is H; $R_{16}$ is Cl; $R_{22}$ is H; $R_{23}$ is H; $R_{24}$ is Br; $R_{25}$ is H; and $R_{26}$ is H;

(r) $R_3$ is $CF_3$; $R_5$ is $NH_2$; Z is $C-R_{16}$; $R_{12}$ is Cl; $R_{13}$ is H; $R_{15}$ is H; $R_{16}$ is Cl; $R_{22}$ is H; $R_{23}$ is Cl; $R_{24}$ is H; $R_{25}$ is Cl; and $R_{26}$ is H;

(s) $R_3$ is $CF_3$; $R_5$ is $NH_2$; Z is $C-R_{16}$; $R_{12}$ is Cl; $R_{13}$ is H; $R_{15}$ is H; $R_{16}$ is Cl; $R_{22}$ is Cl; $R_{23}$ is H; $R_{24}$ is Cl; $R_{25}$ is H; and $R_{26}$ is H;

(t) $R_3$ is $CF_3$; $R_5$ is $NH_2$; Z is $C-R_{16}$; $R_{12}$ is Cl; $R_{13}$ is H; $R_{15}$ is H; $R_{16}$ is Cl; $R_{22}$ is H; $R_{23}$ is $CF_3$; $R_{24}$ is H; $R_{25}$ is H; and $R_{26}$ is H;

(u) $R_3$ is $CF_3$; $R_5$ is $NH_2$; Z is $C-R_{16}$; $R_{12}$ is Cl; $R_{13}$ is H; $R_{15}$ is H; $R_{16}$ is Cl; $R_{22}$ is H; $R_{23}$ is Cl; $R_{24}$ is H; $R_{25}$ is H; and $R_{26}$ is H;

(v) $R_3$ is $CF_3$; $R_5$ is $NH_2$; Z is $C-R_{16}$; $R_{12}$ is Cl; $R_{13}$ is H; $R_{15}$ is H; $R_{16}$ is Cl; $R_{22}$ is H; $R_{23}$ is Br; $R_{24}$ is H; $R_{25}$ is H; and $R_{26}$ is H;

(w) $R_3$ is $CF_3$; $R_5$ is H; Z is $C-R_{16}$; $R_{12}$ is Cl; $R_{13}$ is H; $R_{15}$ is H; $R_{16}$ is Cl; $R_{22}$ and $R_{23}$ together are $(CH=CH)_2$; $R_{24}$ is H; $R_{25}$ is H; and $R_{26}$ is H;

(x) $R_3$ is $CF_3$; $R_5$ is H; Z is $C-R_{16}$; $R_{12}$ is Cl; $R_{13}$ is H; $R_{15}$ is H; $R_{16}$ is Cl; $R_{22}$ is H; $R_{23}$ is H; $R_{24}$ is H; $R_{25}$ is H; and $R_{26}$ is H;

(y) $R_3$ is $CF_3$; $R_5$ is H; Z is $C-R_{16}$; $R_{12}$ is Cl; $R_{13}$ is H; $R_{15}$ is H; $R_{16}$ is Cl; $R_{22}$ is H; $R_{23}$ is H; $R_{24}$ is $CH_3$; $R_{25}$ is H; and $R_{26}$ is H;

(z) $R_3$ is $CF_3$; $R_5$ is H; Z is $C-R_{16}$; $R_{12}$ is Cl; $R_{13}$ is H; $R_{15}$ is H; $R_{16}$ is Cl; $R_{22}$ is H; $R_{23}$ is $NO_2$; $R_{24}$ is H; $R_{25}$ is H; and $R_{26}$ is H;

(a') $R_3$ is $CF_3$; $R_5$ is H; Z is $C-R_{16}$; $R_{12}$ is Cl; $R_{13}$ is H; $R_{15}$ is H; $R_{16}$ is Cl; $R_{22}$ is H; $R_{23}$ is CHO; $R_{24}$ is H; $R_{25}$ is H; and $R_{26}$ is H;

(b') $R_3$ is $CF_3$; $R_5$ is H; Z is $C-R_{16}$; $R_{12}$ is Cl; $R_{13}$ is H; $R_{15}$ is H; $R_{16}$ is Cl; $R_{22}$ is H; $R_{23}$ is $OCH_3$; $R_{24}$ is H; $R_{25}$ is H; and $R_{26}$ is H;

(c') $R_3$ is $CF_3$; $R_5$ is H; Z is $C-R_{16}$; $R_{12}$ is Cl; $R_{13}$ is H; $R_{15}$ is H; $R_{16}$ is Cl; $R_{22}$ is H; $R_{23}$ is H; $R_{24}$ is F; $R_{25}$ is H; and $R_{26}$ is H;

(d') $R_3$ is $CF_3$; $R_5$ is H; Z is $C-R_{16}$; $R_{12}$ is Cl; $R_{13}$ is H; $R_{15}$ is H; $R_{16}$ is Cl; $R_{22}$ is H; $R_{23}$ is F; $R_{24}$ is H; $R_{25}$ is H; and $R_{26}$ is H;

(e') $R_3$ is $CF_3$; $R_5$ is H; Z is $C-R_{16}$; $R_{12}$ is Cl; $R_{13}$ is H; $R_{15}$ is H; $R_{16}$ is Cl; $R_{22}$ is H; $R_{23}$ is Cl; $R_{24}$ is F; $R_{25}$ is H; and $R_{26}$ is H;

(f') $R_3$ is $CF_3$; $R_5$ is H; Z is $C-R_{16}$; $R_{12}$ is Cl; $R_{13}$ is H; $R_{15}$ is H; $R_{16}$ is Cl; $R_{22}$ is H; $R_{23}$ and $R_{24}$ together are $(CH=CH)_2$; $R_{25}$ is H; and $R_{26}$ is H;

(g') $R_3$ is $CF_3$; $R_5$ is H; Z is $C-R_{16}$; $R_{12}$ is Cl; $R_{13}$ is H; $R_{15}$ is H; $R_{16}$ is Cl; $R_{22}$ is H; $R_{23}$ is $NHCOCH_3$; $R_{24}$ is H; $R_{25}$ is H; and $R_{26}$ is H;

(h') $R_3$ is $CF_3$; $R_5$ is H; Z is $C-R_{16}$; $R_{12}$ is Cl; $R_{13}$ is H; $R_{15}$ is H; $R_{16}$ is Cl; $R_{22}$ is CHO; $R_{23}$ is H; $R_{24}$ is H; $R_{25}$ is H; and $R_{26}$ is H;

(i') $R_3$ is $CF_3$; $R_5$ is H; Z is $C-R_{16}$; $R_{12}$ is Cl; $R_{13}$ is H; $R_{15}$ is H; $R_{16}$ is Cl; $R_{22}$ is H; $R_{23}$ is H; $R_{24}$ is CHO; $R_{25}$ is H; and $R_{26}$ is H;

(j') $R_3$ is $CF_3$; $R_5$ is H; Z is $C-R_{16}$; $R_{12}$ is Cl; $R_{13}$ is H; $R_{15}$ is H; $R_{16}$ is Cl; $R_{22}$ is $OCH_3$; $R_{23}$ is H; $R_{24}$ is H; $R_{25}$ is H; and $R_{26}$ is H;

(k') $R_3$ is $SCH_3$; $R_5$ is H; Z is $C-R_{16}$; $R_{12}$ is Cl; $R_{13}$ is H; $R_{15}$ is H; $R_{16}$ is Cl; $R_{22}$ is H; $R_{23}$ is H; $R_{24}$ is $CF_3$; $R_{25}$ is H; and $R_{26}$ is H;

(l') $R_3$ is $SCH_3$; $R_5$ is $NH_2$; Z is $C-R_{16}$; $R_{12}$ is Cl; $R_{13}$ is H; $R_{15}$ is H; $R_{16}$ is Cl; $R_{22}$ is H; $R_{23}$ is H; $R_{24}$ is $CF_3$; $R_{25}$ is H; and $R_{26}$ is H;

(m') $R_3$ is $SOCH_3$; $R_5$ is $NH_2$; Z is $C-R_{16}$; $R_{12}$ is Cl; $R_{13}$ is H; $R_{15}$ is H; $R_{16}$ is Cl; $R_{22}$ is H; $R_{23}$ is H; $R_{24}$ is $CF_3$; $R_{25}$ is H; and $R_{26}$ is H;

(n') $R_3$ is $SOCH_3$; $R_5$ is H; Z is $C-R_{16}$; $R_{12}$ is Cl; $R_{13}$ is H; $R_{15}$ is H; $R_{16}$ is Cl; $R_{22}$ is H; $R_{23}$ is H; $R_{24}$ is $CF_3$; $R_{25}$ is H; and $R_{26}$ is H;

(o') $R_3$ is $SOCH_3$; $R_5$ is Br; Z is $C-R_{16}$; $R_{12}$ is Cl; $R_{13}$ is H; $R_{15}$ is H; $R_{16}$ is Cl; $R_{22}$ is H; $R_{23}$ is H; $R_{24}$ is $CF_3$; $R_{25}$ is H; and $R_{26}$ is H;

(p') $R_3$ is $SCCl_2F$; $R_5$ is H; Z is $C-R_{16}$; $R_{12}$ is Cl; $R_{13}$ is H; $R_{15}$ is H; $R_{16}$ is Cl; $R_{22}$ is H; $R_{23}$ is H; $R_{24}$ is $CF_3$; $R_{25}$ is H; and $R_{26}$ is H;

(q') $R_3$ is $S(O)CCl_2F$; $R_5$ is H; Z is $C-R_{16}$; $R_{12}$ is Cl; $R_{13}$ is H; $R_{15}$ is H; $R_{16}$ is Cl; $R_{22}$ is H; $R_{23}$ is H; $R_{24}$ is $CF_3$; $R_{25}$ is H; and $R_{26}$ is H; or (r') $R_3$ is $S(O)_2CCl_2F$; $R_5$ is H; Z is $C-R_{16}$; $R_{12}$ is Cl; $R_{13}$ is H; $R_{15}$ is H; $R_{16}$ is Cl; $R_{22}$ is H; $R_{23}$ is H; $R_{24}$ is $CF_3$; $R_{25}$ is H; and $R_{26}$ is H.

12. A pesticidal composition comprising:
(a) a pesticidally effective amount of a compound of formula (I):

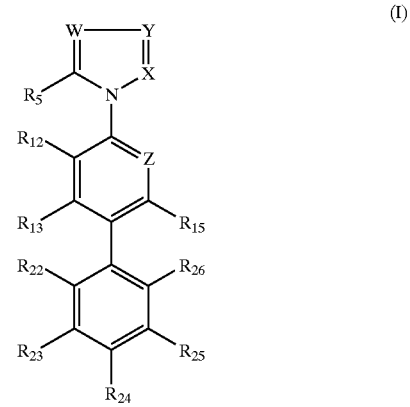

wherein:
X is N;
Y is $C-R_3$;
W is N;
$R_3$ is H, halogen, hydroxy, alkyl, cycloalkyl, haloalkyl, alkoxy, haloalkoxy, CN, $NO_2$, $-S(O)_nR_8$, alkylcarbonyl, alkoxycarbonyl, aminocarbonyl, alkylaminocarbonyl, dialkylaminocarbonyl, hydroxycarbonyl, aminosulfonyl, alkylaminosulfonyl, or dialkylaminosulfonyl;
$R_5$ is hydrogen, halogen, $-NR_9R_{10}$, $-N=CR_{11}R_{19}$, $-S(O)_nR_8$, formyl, alkylcarbonyl, haloalkylcarbonyl, cyano, alkyl, haloalkyl, hydrazino, alkoxycarbonyl, alkyithiocarbonyl, 1H-pyrrol-1-yl or 1H-pyrazol-1-yl;
$R_8$ is alkyl, haloalkyl, alkenyl, or alkynyl, or $R_8$ is a cycloalkyl ring having 3 to 5 carbon atoms;
$R_{11}$ is H or alkyl;
$R_{19}$ is hydrogen, alkyl, haloalkyl, alkoxy, haloalkoxy, alkylthio, amino, monoalkylamino, or dialkylamino; or $R_{19}$ is phenyl, thienyl, pyridyl or furyl, each of which is unsubstituted or substituted with one or more substituents selected from the group consisting of alkyl, haloalkyl, halogen, $NO_2$, CN, alkoxy, haloalkoxy, OH, alkylcarbonyl and alkylcarbonyloxy;

$R_9$ and $R_{10}$, independently of each other, are H, alkyl, haloalkyl, alkylcarbonyl, haloalkylcarbonyl, $R_8S(O)_n$, formyl, alkenyl, alkynyl, alkoxycarbonyl, alkylthiocarbonyl, or aroyl; or $R_9$ and $R_{10}$ are joined so as to together form a divalent radical having 4 to 6 atoms in the chain, said divalent radical being alkylene, alkyleneoxyalkylene or alkyleneaminoalkylene, the alkyl portions of $R_9$ and $R_{10}$ being optionally substituted by $R_7$;

$R_7$ is cyano, nitro, alkoxy, haloalkoxy, $R_8S(O)_n$, —C(O)alkyl, alkoxycarbonyl, aminocarbonyl, alkylaminocarbonyl, dialkylaminocarbonyl, —$CO_2H$, halogen, hydroxy, aminosulfonyl, alkylaminosulfonyl or dialkylaminosulfonyl;

Z is N or C—$R_{16}$;

n is zero, one or two;

$R_{12}$, $R_{13}$, $R_{15}$ and $R_{16}$, independently of one another, are hydrogen, halogen, alkyl, haloalkyl, cyanoalkyl, cyano, nitro, amino, hydrazino, alkoxy, haloalkoxy, alkylsulfenyl, alkylsulfinyl, alkylsulfonyl, haloalkylsulfenyl, haloalkylsulfinyl, haloalkylsulfonyl, formyl, alkylcarbonyl or alkoxycarbonyl;

$R_{22}$, $R_{23}$, $R_{24}$, $R_{25}$, and $R_{26}$; independently of one another, are hydrogen, halogen, alkyl, haloalkyl, cyanoalkyl, cyano, nitro, amino, hydrazino, alkoxy, haloalkoxy, haloalkylcarbonyl, formyl, alkylcarbonyl, thioamide, amide, alkoxycarbonyl, $SF_5$, or $R_8S(O)_n$; or $R_{22}$ and $R_{23}$ or $R_{23}$ and $R_{24}$ or $R_{25}$ and $R_{26}$ together form divinylidene (CH=CH—CH=CH—), methylenedioxy (—O—$CH_2$—O—) or difluoromethylenedioxy (—O—$CF_2$—O—) so as to form a cyclic ring vicinal to the phenyl ring;

or a pesticidally acceptable salt thereof; and (b) a pesticidally acceptable carrier therefor.

13. A composition according to claim 12, comprising from 0.001 to 95% of compound of formula (I).

14. The pesticidal composition according to claim 12 wherein, in the compound of formula (I), $R_3$ is $CF_3$; $R_5$ is $NH_2$; Z is C—$R_{16}$; $R_{12}$ is Cl; $R_{13}$ is H; $R_{15}$ is H; $R_{16}$ is Cl; $R_{22}$ is H; $R_{23}$ is H; $R_{24}$ is Br; $R_{25}$ is H; and $R_{26}$ is H.

15. A pesticidal composition according to claim 12 wherein, in the compound of formula (I), $R_9$ and $R_{10}$ are joined together to form with the adjacent nitrogen atom a morpholine, pyrrolidine, piperidine or piperazine ring, optionally substituted by $R_7$.

16. A pesticidal composition according to claim 12 wherein, in the compound of formula (I), $R_{24}$ is halogen, haloalkyl or haloalkoxy.

17. A pesticidal composition according to claim 12 wherein, in the compound of formula (I), $R_5$ is —$NR_9R_{10}$.

18. A pesticidal composition according to claim 17 wherein, in the compound of formula (I), $R_5$ is —$NH_2$.

19. A pesticidal composition according to claim 12 wherein, in the compound of formula (I), $R_8$ is lower alkyl or haloalkyl.

20. A pesticidal composition according to claim 12 wherein the compound of formula (I) has at least one feature selected from the group consisting of:

$R_3$ is CN or halogen;

$R_5$ is hydrogen, halogen, $C_1$–$C_3$ alkyl, $C_1$–$C_3$ haloalkyl, or —$NR_9R_{10}$;

$R_8$ is methyl, ethyl, —$CF_3$, —$CFCl_2$, or —$CF_2Cl$;

$R_{12}$ and $R_{16}$, independently of each other, are F, Cl, Br or H;

$R_{13}$ and $R_{15}$ are H;

$R_{24}$ is —$CF_3$, —$OCF_3$, —$CHF_2$, —$S(O)_nCF_3$, —$CFCl_2$, —$CF_2Cl$, —$OCF_2Cl$, —$OCFCl_2$, Cl, Br or F; and Z is CCl, CF, CBr or N.

21. A pesticidal composition according to claim 12 wherein, in the compound of formula (I), the $S(O)_nR_8$ substituent is: methylthio, methylsulfinyl, methylsulfonyl, ethylsulfinyl, ethylsulfonyl, ethylthio, cyclopropylsulfinyl, cyclopropylthio, cyclopropylsulfonyl, isopropylsulfinyl, isopropylsulfonyl, isopropylthio, trifluoromethylthio, trifluoromethylsulfinyl, trifluoromethylsulfonyl, dichlorofluoromethylthio, dichlorofluoromethylsulfinyl, dichlorofluoromethylsulfonyl, chlorodifluoromethyithio, chlorodifluoromethylsulfonyl or chlorodifluoromethylsulfinyl.

22. A pesticidal composition according to claim 12 wherein, in the compound of formula (I), the $S(O)_nR_8$ substituent is: trifluoromethylthio, trifluoromethylsulfinyl, trifluoromethylsulfonyl, dichlorofluoromethylthio, dichiorofluoromethylsulfinyl, dichiorofluoromethylsulfonyl, chlorodifluoromethylthio, chiorodifluoromethylsulfonyl or chlorodifluoromethylsulfinyl.

23. A pesticidal composition according to claim 12 wherein, in the compound of formula (I):

(a) $R_3$ is t-butyl; $R_5$ is $NH_2$; Z is C—$R_{16}$; $R_{12}$ is Cl; $R_{13}$ is H; $R_{15}$ is H; $R_{16}$ is Cl; $R_{22}$ is H; $R_{23}$ is H; $R_{24}$ is $CF_3$; $R_{25}$ is H; and $R_{26}$ is H;

(b) $R_3$ is t-butyl; $R_5$ is H; Z is C—$R_{16}$; $R_{12}$ is Cl; $R_{13}$ is H; $R_{15}$ is H; $R_{16}$ is Cl; $R_{22}$ is H; $R_{23}$ is H; $R_{24}$ is $CF_3$; $R_{25}$ is H; and $R_{26}$ is H;

(c) $R_3$ is t-butyl; $R_5$ is Br; Z is C—$R_{16}$; $R_{12}$ is Cl; $R_{13}$ is H; $R_{15}$ is H; $R_{16}$ is Cl; $R_{22}$ is H; $R_{23}$ is H; $R_{24}$ is $CF_3$; $R_{25}$ is H; and $R_{26}$ is H;

(d) $R_3$ is $CF_3$; $R_5$ is $NH_2$; Z is C—$R_{16}$; $R_{12}$ is Cl; $R_{13}$ is H; $R_{15}$ is H; $R_{16}$ is Cl; $R_{22}$ is H; $R_{23}$ is H; $R_{24}$ is $CF_3$; $R_{25}$ is H; and $R_{26}$ is H;

(e) $R_3$ is $CF_3$; $R_5$ is $NH_2$; Z is C—$R_{16}$; $R_{12}$ is Cl; $R_{13}$ is H; $R_{15}$ is H; $R_{16}$ is Cl; $R_{22}$ is H; $R_{23}$ is $NO_2$; $R_{24}$ is H; $R_{25}$ is H; and $R_{26}$ is H;

(f) $R_3$ is $CR_3$; $R_5$ is $NH_2$; Z is C—$R_{16}$; $R_{12}$ is Cl; $R_{13}$ is H; $R_{15}$ is H; $R_{16}$ is Cl; $R_{22}$ is H; $R_{23}$ is F; $R_{24}$ is H; $R_{25}$ is H; and $R_{26}$ is H;

(g) $R_3$ is $CF_3$; $R_5$ is Br; Z is C—$R_{16}$; $R_{12}$ is Cl; $R_{13}$ is H; $R_{15}$ is H; $R_{16}$ is Cl; $R_{22}$ is H; $R_{23}$ is H; $R_{24}$ is $CF_3$; $R_{25}$ is H; and $R_{26}$ is H;

(h) $R_3$ is $CF_3$; $R_5$ is H; Z is C—$R_{16}$; $R_{12}$ is Cl; $R_{13}$ is H; $R_{15}$ is H; $R_{16}$ is Cl; $R_{22}$ is H; $R_{23}$ is H; $R_{24}$ is $CF_3$; $R_{25}$ is H; and $R_{26}$ is H;

(i) $R_3$ is $CF_3$; $R_5$ is $NH_2$; Z is C—$R_{16}$; $R_{12}$ is Cl; $R_{13}$ is H; $R_{15}$ is H; $R_{16}$ is Cl; $R_{22}$ is H; $R_{23}$ and $R_{24}$ together are (CH=CH)$_2$; $R_{25}$ is H; and $R_{26}$ is H;

(j) $R_3$ is $CF_3$; $R_5$ is $NH_2$; Z is C—$R_{16}$; $R_{12}$ is Cl; $R_{13}$ is H; $R_{15}$ is H; $R_{16}$ is Cl; $R_{22}$ and $R_{23}$ together are (CH=CH)$_2$; $R_{24}$ is H; $R_{25}$ is H; and $R_{26}$ is H;

(k) $R_3$ is $CF_3$; $R_5$ is $NH_2$; Z is C—$R_{16}$; $R_{12}$ is Cl; $R_{13}$ is H; $R_{15}$ is H; $R_{16}$ is Cl; $R_{22}$ is $CH_3$; $R_{23}$ is H; $R_{24}$ is H; $R_{25}$ is H; and $R_{26}$ is H;

(l) $R_3$ is $CF_3$; $R_5$ is $NH_2$; Z is C—$R_{16}$; $R_{12}$ is Cl; $R_{13}$ is H; $R_{15}$ is H; $R_{16}$ is Cl; $R_{22}$ is H; $R_{23}$ is $OCH_3$; $R_{24}$ is H; $R_{25}$ is H; and $R_{26}$ is H;

(m) $R_3$ is $CF_3$; $R_5$ is $NH_2$; Z is C—$R_{16}$; $R_{12}$ is Cl; $R_{13}$ is H; $R_{15}$ is H; $R_{16}$ is Cl; $R_{22}$ is H; $R_{23}$ is H; $R_{24}$ is $OCH_3$; $R_{25}$ is H; and $R_{26}$ is H;

(n) $R_3$ is $CF_3$; $R_5$ is $NH_2$; Z is $C-R_{16}$; $R_{12}$ is Cl; $R_{13}$ is H; $R_{15}$ is H; $R_{16}$ is Cl; $R_{22}$ is H; $R_{23}$ is H; $R_{24}$ is $SCH_3$; $R_{25}$ is H; and $R_{26}$ is H;

(o) $R_3$ is $CF_3$; $R_5$ is $NH_2$; Z is $C-R_{16}$; $R_{12}$ is Cl; $R_{13}$ is H; $R_{15}$ is H; $R_{16}$ is Cl; $R_{22}$ is H; $R_{23}$ is H; $R_{24}$ is F; $R_{25}$ is H; and $R_{26}$ is H;

(p) $R_3$ is $CF_3$; $R_5$ is $NH_2$; Z is $C-R_{16}$; $R_{12}$ is Cl; $R_{13}$ is H; $R_{15}$ is H; $R_{16}$ is Cl; $R_{22}$ is H; $R_{23}$ is H; $R_{24}$ is Cl; $R_{25}$ is H; and $R_{26}$ is H;

(q) $R_3$ is $CF_3$; $R_5$ is $NH_2$; Z is $C-R_{16}$; $R_{12}$ is Cl; $R_{13}$ is H; $R_{15}$ is H; $R_{16}$ is Cl; $R_{22}$ is H; $R_{23}$ is H; $R_{24}$ is Br; $R_{25}$ is H; and $R_{26}$ is H;

(r) $R_3$ is $CF_3$; $R_5$ is $NH_2$; Z is $C-R_{16}$; $R_{12}$ is Cl; $R_{13}$ is H; $R_{15}$ is H; $R_{16}$ is Cl; $R_{22}$ is H; $R_{23}$ is Cl; $R_{24}$ is H; $R_{25}$ is Cl; and $R_{26}$ is H;

(s) $R_3$ is $CF_3$; $R_5$ is $NH_2$; Z is $C-R_{16}$; $R_{12}$ is Cl; $R_{13}$ is H; $R_{15}$ is H; $R_{16}$ is Cl; $R_{22}$ is Cl; $R_{23}$ is H; $R_{24}$ is Cl; $R_{25}$ is H; and $R_{26}$ is H;

(t) $R_3$ is $CF_3$; $R_5$ is $NH_2$; Z is $C-R_{16}$; $R_{12}$ is Cl; $R_{13}$ is H; $R_{15}$ is H; $R_{16}$ is Cl; $R_{22}$ is H; $R_{23}$ is $CF_3$; $R_{24}$ is H; $R_{25}$ is H; and $R_{26}$ is H;

(u) $R_3$ is $CF_3$; $R_5$ is $NH_2$; Z is $C-R_{16}$; $R_{12}$ is Cl; $R_{13}$ is H; $R_{15}$ is H; $R_{16}$ is Cl; $R_{22}$ is H; $R_{23}$ is Cl; $R_{24}$ is H; $R_{25}$ is H; and $R_{26}$ is H;

(v) $R_3$ is $CF_3$; $R_5$ is $NH_2$; Z is $C-R_{16}$; $R_{12}$ is Cl; $R_{13}$ is H; $R_{15}$ is H; $R_{16}$ is Cl; $R_{22}$ is H; $R_{23}$ is Br; $R_{24}$ is H; $R_{25}$ is H; and $R_{26}$ is H;

(w) $R_3$ is $CF_3$; $R_5$ is H; Z is $C-R_{16}$; $R_{12}$ is Cl; $R_{13}$ is H; $R_{15}$ is H; $R_{16}$ is Cl; $R_{22}$ and $R_{23}$ together are $(CH=CH)_2$; $R_{24}$ is H; $R_{25}$ is H; and $R_{26}$ is H;

(x) $R_3$ is $CF_3$; $R_5$ is H; Z is $C-R_{16}$; $R_{12}$ is Cl; $R_{13}$ is H; $R_{15}$ is H; $R_{16}$ is Cl; $R_{22}$ is H; $R_{23}$ is H; $R_{24}$ is H; $R_{25}$ is H; and $R_{26}$ is H;

(y) $R_3$ is $CF_3$; $R_5$ is H; Z is $C-R_{16}$; $R_{12}$ is Cl; $R_{13}$ is H; $R_{15}$ is H; $R_{16}$ is Cl; $R_{22}$ is H; $R_{23}$ is H; $R_{24}$ is $CH_3$; $R_{25}$ is H; and $R_{26}$ is H;

(z) $R_3$ is $CF_3$; $R_5$ is H; Z is $C-R_{16}$; $R_{12}$ is Cl; $R_{13}$ is H; $R_{15}$ is H; $R_{16}$ is Cl; $R_{22}$ is H; $R_{23}$ is $NO_2$; $R_{24}$ is H; $R_{25}$ is H; and $R_{26}$ is H;

(a') $R_3$ is $CF_3$; $R_5$ is n; Z is $C-R_{16}$; $R_{12}$ is Cl; $R_{13}$ is H; $R_{15}$ is H; $R_{16}$ is Cl; $R_{22}$ is H; $R_{23}$ is CHO; $R_{24}$ H; $R_{25}$ is H; and $R_{26}$ is H;

(b') $R_3$ is $CF_3$; $R_5$ is H; Z is $C-R_{16}$; $R_{12}$ is Cl; $R_{13}$ is H; $R_{15}$ is H; $R_{16}$ is Cl; $R_{22}$ is H; $R_{23}$ is $OCH_3$; $R_{24}$ is H; $R_{25}$ is H; and $R_{26}$ is H;

(c') $R_3$ is $CF_3$; $R_5$ is H; Z is $C-R_{16}$; $R_{12}$ is Cl; $R_{13}$ is H; $R_{15}$ is H; $R_{16}$ is Cl; $R_{22}$ is H; $R_{23}$ is H; $R_{24}$ is F; $R_{25}$ is H; and $R_{26}$ is H;

(d') $R_3$ is $CF_3$; $R_5$ is H; Z is $C-R_{16}$; $R_{12}$ is Cl; $R_{13}$ is H; $R_{15}$ is H; $R_{16}$ is Cl; $R_{22}$ is H; $R_{23}$ is F; $R_{24}$ is H; $R_{25}$ is H; and $R_{26}$ is H;

(e') $R_3$ is $CF_3$; $R_5$ is H; Z is $C-R_{16}$; $R_{12}$ is Cl; $R_{13}$ is H; $R_{15}$ is H; $R_{16}$ is Cl; $R_{22}$ is H; $R_{23}$ is Cl; $R_{24}$ is F; $R_{25}$ is H; and $R_{26}$ is H;

(f') $R_3$ is $CF_3$; $R_5$ is H; Z is $C-R_{16}$; $R_{12}$ is Cl; $R_{13}$ is H; $R_{15}$ is H; $R_{16}$ is Cl; $R_{22}$ is H; $R_{23}$ and $R_{24}$ together are $(CH=CH)_2$; $R_{25}$ is H; and $R_{26}$ is H;

(g') $R_3$ is $CF_3$; $R_5$ is H; Z is $C-R_{16}$; $R_{12}$ is Cl; $R_{13}$ is H; $R_{15}$ is H; $R_{16}$ is Cl; $R_{22}$ is H; $R_{23}$ is $NHCOCH_3$; $R_{24}$ is H; $R_{25}$ is H; and $R_{26}$ is H;

(h') $R_3$ is $CF_3$; $R_5$ is H; Z is $C-R_{16}$; $R_{12}$ is Cl; $R_{13}$ is H; $R_{15}$ is H; $R_{16}$ is Cl; $R_{22}$ is CHO; $R_{23}$ is H; $R_{24}$ is H; $R_{25}$ is H; and $R_{26}$ is H;

(i') $R_3$ is $CF_3$; $R_5$ is H; Z is $C-R_{16}$; $R_{12}$ is Cl; $R_{13}$ is H; $R_{15}$ is H; $R_{16}$ is Cl; $R_{22}$ is H; $R_{23}$ is H; $R_{24}$ is CHO; $R_{25}$ is H; and $R_{26}$ is H;

(j') $R_3$ is $CF_3$; $R_5$ is H; Z is $C-R_{16}$; $R_{12}$ is Cl; $R_{13}$ is H; $R_{15}$ is H; $R_{16}$ is Cl; $R_{22}$ is $OCH_3$; $R_{23}$ is H; $R_{24}$ is H; $R_{25}$ is H; and $R_{26}$ is H;

(k') $R_3$ is $SCH_3$; $R_5$ is H; Z is $C-R_{16}$; $R_{12}$ is Cl; $R_{13}$ is H; $R_{15}$ is H; $R_{16}$ is Cl; $R_{22}$ is H; $R_{23}$ is H; $R_{24}$ is $CF_3$; $R_{25}$ is H; and $R_{26}$ is H;

(l') $R_3$ is $SCH_3$; $R_5$ is $NH_2$; Z is $C-R_{16}$; $R_{12}$ is Cl; $R_{13}$ is H; $R_{15}$ is H; $R_{16}$ is Cl; $R_{22}$ is H; $R_{23}$ is H; $R_{24}$ is $CF_3$; $R_{25}$ is H; and $R_{26}$ is H;

(m') $R_3$ is $SOCH_3$; $R_5$ is $NH_2$; Z is $C-R_{16}$; $R_{12}$ is Cl; $R_{13}$ is H; $R_{15}$ is H; $R_{16}$ is Cl; $R_{22}$ is H; $R_{23}$ is H; $R_{24}$ is $CF_3$; $R_{25}$ is H; and $R_{26}$ is H;

(n') $R_3$ is $SOCH_3$; $R_5$ is H; Z is $C-R_{16}$; $R_{12}$ is Cl; $R_{13}$ is H; $R_{15}$ is H; $R_{16}$ is Cl; $R_{22}$ is H; $R_{23}$ is H; $R_{24}$ is $CF_3$; $R_{25}$ is H; and $R_{26}$ is H;

(o') $R_3$ is $SOCH_3$; $R_5$ is Br; Z is $C-R_{16}$; $R_{12}$ is Cl; $R_{13}$ is H; $R_{15}$ is H; $R_{16}$ is Cl; $R_{22}$ is H; $R_{23}$ is H; $R_{24}$ is $CF_3$; $R_{25}$ is H; and $R_{26}$ is H;

(p') $R_3$ is $SCCl_2F$; $R_5$ is H; Z is $C-R_{16}$; $R_{12}$ is Cl; $R_{13}$ is H; $R_{15}$ is H; $R_{16}$ is Cl; $R_{22}$ is H; $R_{23}$ is H; $R_{24}$ is $CF_3$; $R_{25}$ is H; and $R_{26}$ is H;

(q') $R_3$ is $S(O)CCl_2F$; $R_5$ is H; Z is $C-R_{16}$; $R_{12}$ is Cl; $R_{13}$ is H; $R_{15}$ is H; $R_{16}$ is Cl; $R_{22}$ is H; $R_{23}$ is H; $R_{24}$ is $CF_3$; $R_{25}$ is H; and $R_{26}$ is H; or (r') $R_3$ is $S(O)_2CCl_2F$; $R_5$ is H; Z is $C-R_{16}$; $R_{12}$ is Cl; $R_{13}$ is H; $R_{15}$ is H; $R_{16}$ is Cl; $R_{22}$ is H; $R_{23}$ is H; $R_{24}$ is $CF_3$; $R_{25}$ is H; and $R_{26}$ is H.

24. A method for controlling pests at a locus comprising applying to said locus a pesticidally effective amount of a compound of formula (I):

(I)

wherein:
X is N;
Y is $C-R_3$;
W is N;
$R_3$ is H, halogen, hydroxy, alkyl, cycloalkyl, haloalkyl, alkoxy, haloalkoxy, CN, $NO_2$, $-S(O)_nR_8$, alkylcarbonyl, alkoxycarbonyl, aminocarbonyl, alkylaminocarbonyl, dialkylaminocarbonyl, hydroxycarbonyl, aminosulfonyl, alkylaminosulfonyl, or dialkylaminosulfonyl;
$R_5$ is hydrogen, halogen, $-NR_9R_{10}$, $-N=CR_{11}R_{19}$, $-S(O)_nR_8$, formyl, alkylcarbonyl, haloalkylcarbonyl, cyano, alkyl, haloalkyl, hydrazino, alkoxycarbonyl, alkyithiocarbonyl, 1H-pyrrol-1-yl or 1H-pyrazol-1-yl;

$R_8$ is alkyl, haloalkyl, alkenyl, or alkynyl, or $R_8$ is a cycloalkyl ring having 3 to 5 carbon atoms;

$R_{11}$ is H or alkyl;

$R_{19}$ is hydrogen, alkyl, haloalkyl, alkoxy, haloalkoxy, alkylthio, amino, monoalkylamino, or dialkylamino; or $R_{19}$ is phenyl, thienyl, pyridyl or furyl, each of which is unsubstituted or substituted with one or more substituents selected from the group consisting of alkyl, haloalkyl, halogen, $NO_2$, CN, alkoxy, haloalkoxy, OH, alkylcarbonyl and alkylcarbonyloxy;

$R_9$ and $R_{10}$, independently of each other, are H, alkyl, haloalkyl, alkylcarbonyl, haloalkylcarbonyl, $R_8S(O)_n$, formyl, alkenyl, alkynyl, alkoxycarbonyl, alkylthiocarbonyl, or aroyl; or $R_9$ and $R_{10}$ are joined so as to together form a divalent radical having 4 to 6 atoms in the chain, said divalent radical being alkylene, alkyleneoxyalkylene or alkyleneaminoalkylene, the alkyl portions of $R_9$ and $R_{10}$ being optionally substituted by $R_7$;

$R_7$ is cyano, nitro, alkoxy, haloalkoxy, $R_8S(O)_n$, —C(O)alkyl, alkoxycarbonyl, aminocarbonyl, alkylaminocarbonyl, dialkylaminocarbonyl, —$CO_2H$, halogen, hydroxy, aminosulfonyl, alkylaminosulfonyl or dialkylaminosulfonyl;

Z is N or C—$R_{16}$;

n is zero, one or two;

$R_{12}$, $R_{13}$, $R_{15}$ and $R_{16}$, independently of one another, are hydrogen, halogen, alkyl, haloalkyl, cyanoalkyl, cyano, nitro, amino, hydrazino, alkoxy, haloalkoxy, alkylsulfenyl, alkylsulfinyl, alkylsulfonyl, haloalkylsulfenyl, haloalkylsulfinyl, haloalkylsulfonyl, formyl, alkylcarbonyl or alkoxycarbonyl;

$R_{22}$, $R_{23}$, $R_{24}$, $R_{25}$, and $R_{26}$; independently of one another, are hydrogen, halogen, alkyl, haloalkyl, cyanoalkyl, cyano, nitro, amino, hydrazino, alkoxy, haloalkoxy, haloalkylcarbonyl, formyl, alkylcarbonyl, thioamide, amide, alkoxycarbonyl, $SF_5$, or $R_8S(O)_n$; or $R_{22}$ and $R_{23}$ or $R_{23}$ and $R_{24}$ or $R_{25}$ and $R_{26}$ together form divinylidene (CH=CH—CH=CH—), methylenedioxy (—O—$CH_2$—O—) or difluoromethylenedioxy (—O—$CF_2$—O—) so as to form a cyclic ring vicinal to the phenyl ring;

or a pesticidally acceptable salt thereof.

25. A method according to claim 24, wherein said pests are insects and wherein said pesticidally effective amount is an insecticidally effective amount.

26. A method according to claim 25, comprising applying to said locus from about 0.01 to about 2 kg/ha of compound of formula (I).

27. A method according to claim 26, comprising applying to said locus from about 0.1 to about 1 kg/ha of compound of formula (I).

28. A method for controlling pests at a locus comprising applying to said locus a pesticidally effective amount of a composition as claimed in claim 12.

29. A method according to claim 28, wherein said pests are insects and wherein said pesticidally effective amount is an insecticidally effective amount.

30. The method according to claim 24 wherein, in the compound of formula (I), $R_3$ is $CF_3$; $R_5$ is $NH_2$; Z is C—$R_{16}$; $R_{12}$ is Cl; $R_{13}$ is H; $R_{15}$ is H; $R_{16}$ is Cl; $R_{22}$ is H; $R_{23}$ is H; $R_{24}$ is Br; $R_{25}$ is H; and $R_{26}$ is H.

31. A method according to claim 24 wherein, in the compound of formula (I), $R_9$ and $R_{10}$ are joined together to form with the adjacent nitrogen atom a morpholine, pyrrolidine, piperidine or piperazine ring, optionally substituted by $R_7$.

32. A method according to claim 24 wherein, in the compound of formula (I), $R_{24}$ is halogen, haloalkyl or haloalkoxy.

33. A method according to claim 24 wherein, in the compound of formula (I), $R_5$ is —$NR_9R_{10}$.

34. A method according to claim 33 wherein, in the compound of formula (I), $R_5$ is —$NH_2$.

35. A method according to claim 24 wherein, in the compound of formula (I), $R_8$ is lower alkyl or haloalkyl.

36. A method according to claim 24, wherein the compound of formula (I) has at least one feature selected from the group consisting of:

$R_3$ is CN or halogen;

$R_5$ is hydrogen, halogen, $C_1$–$C_3$ alkyl, $C_1$–$C_3$ haloalkyl, or —$NR_9R_{10}$;

$R_8$ is methyl, ethyl, —$CF_3$, —$CFCl_2$, or —$CF_2Cl$;

$R_{12}$ and $R_{16}$, independently of each other, are F, Cl, Br or H; $R_{13}$ and $R_{15}$ are H;

$F_{24}$ is —$CF_3$, —$OCF_3$, —$CHF_2$, —$S(O)_nCF_3$, —$CFCl_2$, —$CF_2Cl$, —$OCF_2Cl$, —$OCFCl_2$, Cl, Br or F; and Z is CCl, CF, CBr or N.

37. A method according to claim 24 wherein, in the compound of formula (I), the $S(O)_nR_8$ substituent is: methylthio, methylsulfinyl, methylsulfonyl, ethylsulfinyl, ethylsulfonyl, ethylthio, cyclopropylsulfinyl, cyclopropylthio, cyclopropylsulfonyl, isopropylsulfinyl, isopropylsulfonyl, isopropylthio, trifluoromethylthio, trifluoromethylsulfinyl, trifluoromethylsulfonyl, dichlorofluoromethylthio, dichlorofluoromethylsulfinyl dichlorofluoromethylsulfonyl chlorodifluoromethylthio, chlorodifluoromethylsulfonyl or chlorodifluoromethylsulfinyl.

38. A method according to claim 24 wherein, in the compound of formula (I), the $S(O)_nR_8$ substituent is: trifluoromethylthio, trifluoromethylsulfinyl, trifluoromethylsulfonyl, dichlorofluoromethylthio, dichlorofluoromethylsulfinyl, dichlorofluoromethylsulfonyl, chlorodifluoromethylthio, chlorodifluoromethylsulfonyl or chlorodifluoromethylsulfinyl.

39. A method according to claim 24 wherein, in the compound of formula (I):

(a) $R_3$ is t-butyl; $R_5$ is $NH_2$; Z is C—$R_{16}$; $R_{12}$ is Cl, $R_{13}$ is H; $R_{15}$ is H; $R_{16}$ is Cl; $R_{22}$ is H; $R_{23}$ is H; $R_{24}$ is $CF_3$; $R_{25}$ is H; and $R_{26}$ is H;

(b) $R_3$ is t-butyl; $R_5$ is H; Z is C—$R_{16}$; $R_{12}$ is Cl; $R_{13}$ is H; $R_{15}$ is H; $R_{16}$ is Cl; $R_{22}$ is H; $R_{23}$ is H; $R_{24}$ is $CF_3$; $R_{25}$ is H; and $R_{26}$ is H;

(c) $R_3$ is t-butyl; $R_5$ is Br; Z is C—$R_{16}$; $R_{12}$ is Cl; $R_{13}$ is H; $R_{15}$ is H; $R_{16}$ is Cl; $R_{22}$ is H; $R_{23}$ is H; $R_{24}$ is $CF_3$; $R_{25}$ is H; and $R_{26}$ is H;

(d) $R_3$ is $CF_3$; $R_5$ is $NH_2$; Z is C—$R_{16}$; $R_{12}$ is Cl; $R_{13}$ is H; $R_{15}$ is H; $R_{16}$ is Cl; $R_{22}$ is H; $R_{23}$ is H; $R_{24}$ is $CF_3$; $R_{25}$ is H; and $R_{26}$ is H;

(e) $R_3$ is $CF_3$; $R_5$ is $NH_2$; Z is C—$R_{16}$; $R_{12}$ is Cl; $R_{13}$ is H; $R_{15}$ is H; $R_{16}$ is Cl; $R_{22}$ is H; $R_{23}$ is $NO_2$; $R_{24}$ is H; $R_{25}$ is H; and $R_{26}$ is H;

(f) $R_3$ is $CF_3$; $R_5$ is $NH_2$; Z is C—$R_{16}$; $R_{12}$ is Cl; $R_{13}$ is H; $R_{15}$ is H; $R_{16}$ is Cl; $R_{22}$ is H; $R_{23}$ is F; $R_{24}$ is H; $R_{25}$ is H; and $R_{26}$ is H;

(g) $R_3$ is $CF_3$; $R_5$ is Br; Z is C—$R_{16}$; $R_{12}$ is Cl; $R_{13}$ is H; $R_{15}$ is H; $R_{16}$ is Cl; $R_{22}$ is H; $R_{23}$ is H; $R_{24}$ is $CF_3$; $R_{25}$ is H; and $R_{26}$ is H;

(h) $R_3$ is $CF_3$; $R_5$ is H; Z is C—$R_{16}$; $R_{12}$ is Cl; $R_{13}$ is H; $R_{15}$ is H; $R_{16}$ is Cl; $R_{22}$ is H; $R_{23}$ is H; $R_{24}$ is $CF_3$; $R_{25}$ is H; and $R_{26}$ is H;

(i) $R_3$ is $CF_3$; $R_5$ is $NH_2$; Z is C—$R_{16}$; $R_{12}$ is Cl; $R_{13}$ is H; $R_{15}$ is H; $R_{16}$ is Cl; $R_{22}$ is H; $R_{23}$ and $R_{24}$ together are (CH=CH)$_2$; $R_{25}$ is H; and $R_{26}$ is H;

(j) $R_3$ is $CF_3$; $R_5$ is $NH_2$; Z is C—$R_{16}$; $R_{12}$ is Cl; $R_{13}$ is H; $R_{15}$ is H; $R_{16}$ is Cl; $R_{22}$ and $R_{23}$ together are (CH=CH)$_2$; $R_{24}$ is H; $R_{25}$ is H; and $R_{26}$ is H;

(k) $R_3$ is $CF_3$; $R_5$ is $NH_2$; Z is C—$R_{16}$; $R_{12}$ is Cl; $R_{13}$ is H; $R_{15}$ is H; $R_{16}$ is Cl; $R_{22}$ is $CH_3$; $R_{23}$ is H; $R_{24}$ is H; $R_{25}$ is H; and $R_{26}$ is H;

(l) $R_3$ is $CF_3$; $R_5$ is $NH_2$; Z is C—$R_{16}$; $R_{12}$ is Cl; $R_{13}$ is H; $R_{15}$ is H; $R_{16}$ is Cl; $R_{22}$ is H; $R_{23}$ is $OCH_3$; $R_{24}$ is H; $R_{25}$ is H; and $R_{26}$ is H;

(m) $R_3$ is $CF_3$; $R_5$ is $NH_2$; Z is C—$R_{16}$; $R_{12}$ is Cl; $R_{13}$ is H; $R_{15}$ is H; $R_{16}$ is Cl; $R_{22}$ is H; $R_{23}$ is H; $R_{24}$ is $OCH_3$; $R_{25}$ is H; and $R_{26}$ is H;

(n) $R_3$ is $CF_3$; $R_5$ is $NH_2$; Z is C—$R_{16}$; $R_{12}$ is Cl; $R_{13}$ is H; $R_{15}$ is H; $R_{16}$ is Cl; $R_{22}$ is H; $R_{23}$ is H; $R_{24}$ is $SCH_3$; $R_{25}$ is H; and $R_{26}$ is H;

(o) $R_3$ is $CF_3$; $R_5$ is $NH_2$; Z is C—$R_{16}$; $R_{12}$ is Cl; $R_{13}$ is H; $R_{15}$ is H; $R_{16}$ is Cl; $R_{22}$ is H; $R_{23}$ is H; $R_{24}$ is F; $R_{25}$ is H; and $R_{26}$ is H;

(p) $R_3$ is $CF_3$; $R_5$ is $NH_2$; Z is C—$R_{16}$; $R_{12}$ is Cl; $R_{13}$ is H; $R_{15}$ is H; $R_{16}$ is Cl; $R_{22}$ is H; $R_{23}$ is H; $R_{24}$ is Cl; $R_{25}$ is H; and $R_{26}$ is H;

(q) $R_3$ is $CF_3$; $R_5$ is $NH_2$; Z is C—$R_{16}$; $R_{12}$ is Cl; $R_{13}$ is H; $R_{15}$ is H; $R_{16}$ is Cl; $R_{22}$ is H; $R_{23}$ is H; $R_{24}$ is Br; $R_{25}$ is H; and $R_{26}$ is H;

(r) $R_3$ is $CF_3$; $R_5$ is $NH_2$; Z is C—$R_{16}$; $R_{12}$ is Cl; $R_{13}$ is H; $R_{15}$ is H; $R_{16}$ is Cl; $R_{22}$ is H; $R_{23}$ is Cl; $R_{24}$ is H; $R_{25}$ is Cl; and $R_{26}$ is H;

(s) $R_3$ is $CF_3$; $R_5$ is $NH_2$; Z is C—$R_{16}$; $R_{12}$ is Cl; $R_{13}$ is H; $R_{15}$ is H; $R_{16}$ is Cl; $R_{22}$ is Cl; $R_{23}$ is H; $R_{24}$ is Cl; $R_{25}$ is H; and $R_{26}$ is H;

(t) $R_3$ is $CF_3$; $R_5$ is $NH_2$; Z is C—$R_{16}$; $R_{12}$ is Cl; $R_{13}$ is H; $R_{15}$ is H; $R_{16}$ is Cl; $R_{22}$ is H; $R_{23}$ is $CF_3$; $R_{24}$ is H; $R_{25}$ is H; and $R_{26}$ is H;

(u) $R_3$ is $CF_3$; $R_5$ is $NH_2$; Z is C—$R_{16}$; $R_{12}$ is Cl; $R_{13}$ is H; $R_{15}$ is H; $R_{16}$ is Cl; $R_{22}$ is H; $R_{23}$ is Cl; $R_{24}$ is H; $R_{25}$ is H; and $R_{26}$ is H;

(v) $R_3$ is $CF_3$; $R_5$ is $NH_2$; Z is C—$R_{16}$; $R_{12}$ is Cl; $R_{13}$ is H; $R_{15}$ is H; $R_{16}$ is Cl; $R_{22}$ is H; $R_{23}$ is Br; $R_{24}$ is H; $R_{25}$ is H; and $R_{26}$ is H;

(w) $R_3$ is $CF_3$; $R_5$ is H; Z is C—$R_{16}$; $R_{12}$ is Cl; $R_{13}$ is H; $R_{15}$ is H; $R_{16}$ is Cl; $R_{22}$ and $R_{23}$ together are (CH=CH)$_2$; $R_{24}$ is H; $R_{25}$ is H; and $R_{26}$ is H;

(x) $R_3$ is $CF_3$; $R_5$ is H; Z is C—$R_{16}$; $R_{12}$ is Cl; $R_{13}$ is H; $R_{15}$ is H; $R_{16}$ is Cl; $R_{22}$ is H; $R_{23}$ is H; $R_{24}$ is H; $R_{25}$ is H; and $R_{26}$ is H;

(y) $R_3$ is $CF_3$; $R_5$ is H; Z is C—$R_{16}$; $R_{12}$ is Cl; $R_{13}$ is H; $R_{15}$ is H; $R_{16}$ is Cl; $R_{22}$ is H; $R_{23}$ is H; $R_{24}$ is $CH_3$; $R_{25}$ is H; and $R_{26}$ is H;

(z) $R_3$ is $CF_3$; $R_5$ is H; Z is C—$R_{16}$; $R_{12}$ is Cl; $R_{13}$ is H; $R_{15}$ is H; $R_{16}$ is Cl; $R_{22}$ is H; $R_{23}$ is $NO_2$; $R_{24}$ is H; $R_{25}$ is H; and $R_{26}$ is H;

(a') $R_3$ is $CF_3$; $R_5$ is H; Z is C—$R_{16}$; $R_{12}$ is Cl; $R_{13}$ is H; $R_{15}$ is H; $R_{16}$ is Cl; $R_{22}$ is H; $R_{23}$ is CHO; $R_{24}$ is H; $R_{25}$ is H; and $R_{26}$ is H;

(b') $R_3$ is $CF_3$; $R_5$ is H; Z is C—$R_{16}$; $R_{12}$ is Cl; $R_{13}$ is H; $R_{15}$ is H; $R_{16}$ is Cl; $R_{22}$ is H; $R_{23}$ is $OCH_3$; $R_{24}$ is H; $R_{25}$ is H; and $R_{26}$ is H;

(c') $R_3$ is $CF_3$; $R_5$ is H; Z is C—$R_{16}$; $R_{12}$ is Cl; $R_{13}$ is H; $R_{15}$ is H; $R_{16}$ is Cl; $R_{22}$ is H; $R_{23}$ is H; $R_{24}$ is F; $R_{25}$ is H; and $R_{26}$ is H;

(d') $R_3$ is $CF_3$; $R_5$ is H; Z is C—$R_{16}$; $R_{12}$ is Cl; $R_{13}$ is H; $R_{15}$ is H; $R_{16}$ is Cl; $R_{22}$ is H; $R_{23}$ is F; $R_{24}$ is H; $R_{25}$ is H; and $R_{26}$ is H;

(e') $R_3$ is $CF_3$; $R_5$ is H; Z is C—$R_{16}$; $R_{12}$ is Cl; $R_{13}$ is H; $R_{15}$ is H; $R_{16}$ is Cl; $R_{22}$ is H; $R_{23}$ is Cl; $R_{24}$ is F; $R_{25}$ is H; and $R_{26}$ is H;

(f') $R_3$ is $CF_3$; $R_5$ is H; Z is C—$R_{16}$; $R_{12}$ is Cl; $R_{13}$ is H; $R_{15}$ is H; $R_{16}$ is Cl; $R_{22}$ is H; $R_{23}$ and $R_{24}$ together are (CH=CH)$_2$; $R_{25}$ is H; and $R_{26}$ is H;

(g') $R_3$ is $CF_3$; $R_5$ is H; Z is C—$R_{16}$; $R_{12}$ is Cl; $R_{13}$ is H; $R_{15}$ is H; $R_{16}$ is Cl; $R_{22}$ is H; $R_{23}$ is $NHCOCH_3$; $R_{24}$ is H; $R_{25}$ is H; and $R_{26}$ is H;

(h') $R_3$ is $CF_3$; $R_5$ is H; Z is C—$R_{16}$; $R_{12}$ is Cl; $R_{13}$ is H; $R_{15}$ is H; $R_{16}$ is Cl; $R_{22}$ is CHO; $R_{23}$ is H; $R_{24}$ is H; $R_{25}$ is H; and $R_{26}$ is H;

(i') $R_3$ is $CF_3$; $R_5$ is H; Z is C—$R_{16}$; $R_{12}$ is Cl; $R_{13}$ is H; $R_{15}$ is H; $R_{16}$ is Cl; $R_{22}$ is H; $R_{23}$ is H; $R_{24}$ is CHO; $R_{25}$ is H; and $R_{26}$ is H;

(j') $R_3$ is $CF_3$; $R_5$ is H; Z is C—$R_{16}$; $R_{12}$ is Cl; $R_{13}$ is H; $R_{15}$ is H; $R_{16}$ is Cl; $R_{22}$ is $OCH_3$; $R_{23}$ is H; $R_{24}$ is H; $R_{25}$ is H; and $R_{26}$ is H;

(k') $R_3$ is $SCH_3$; $R_5$ is H; Z is C—$R_{16}$; $R_{12}$ is Cl; $R_{13}$ is H; $R_{15}$ is H; $R_{16}$ is Cl; $R_{22}$ is H; $R_{23}$ is H; $R_{24}$ is $CF_3$; $R_{25}$ is H; and $R_{26}$ is H;

(l') $R_3$ is $SCH_3$; $R_5$ is $NH_2$; Z is C—$R_{16}$; $R_{12}$ is Cl; $R_{13}$ is H; $R_{15}$ is H; $R_{16}$ is Cl; $R_{22}$ is H; $R_{23}$ is H; $R_{24}$ is $CF_3$; $R_{25}$ is H; and $R_{26}$ is H;

(m') $R_3$ is $SOCH_3$; $R_5$ is $NH_2$; Z is C—$R_{16}$; $R_{12}$ is Cl; $R_{13}$ is H; $R_{15}$ is H; $R_{16}$ is Cl; $R_{22}$ is H; $R_{23}$ is H; $R_{24}$ is $CF_3$; $R_{25}$ is H; and $R_{26}$ is H;

(n') $R_3$ is $SOCH_3$; $R_5$ is H; Z is C—$R_{16}$; $R_{12}$ is Cl; $R_{13}$ is H; $R_{15}$ is H; $R_{16}$ is Cl; $R_{22}$ is H; $R_{23}$ is H; $R_{24}$ is $CF_3$; $R_{25}$ is H; and $R_{26}$ is H;

(o') $R_3$ is $SOCH_3$; $R_5$ is Br; Z is C—$R_{16}$; $R_{12}$ is Cl; 13 is H; $R_{15}$ is H; $R_{16}$ is Cl; $R_{22}$ is H; $R_{23}$ is H; $R_{24}$ is $CF_3$; $R_{25}$ is H; and $R_{26}$ is H;

(p') $R_3$ is $SCCl_2F$; $R_5$ is H; Z is C—$R_{16}$; $R_{12}$ is Cl; $R_{13}$ is H; $R_{15}$ is H; $R_{16}$ is Cl; $R_{22}$ is H; $R_{23}$ is H; $R_{24}$ is $CF_3$; $R_{25}$ is H; and $R_{26}$ is H;

(q') $R_3$ is $S(O)CCl_2F$; $R_5$ is H; Z is C—$R_{16}$; $R_{12}$ is Cl; $R_{13}$ is H; $R_{15}$ is H; $R_{16}$ is Cl; $R_{22}$ is H; $R_{23}$ is H; $R_{24}$ is $CF_3$; $R_{25}$ is H; and $R_{26}$ is H; or (r') $R_3$ is $S(O)_2CCl_2F$; $R_5$ is H; Z is C—$R_{16}$; $R_{12}$ is Cl; $R_{13}$ is H; $R_{15}$ is H; $R_{16}$ is Cl; $R_{22}$ is H; $R_{23}$ is H; $R_{24}$ is $CF_3$; $R_{25}$ is H; and $R_{26}$ is H.

40. A process for preparing a compound of formula (I) according to claim 1, which comprises:

(a) reacting a compound of formula (II):

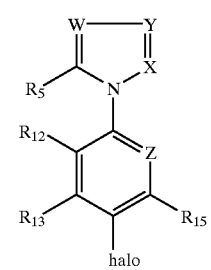

(II)

wherein W, X, Y, Z, $R_5$, $R_{12}$, $R_{13}$ and $R_{15}$ are as defined in claim 1, with a boric acid or ester in the presence of a coupling catalyst to form a compound of formula (III):

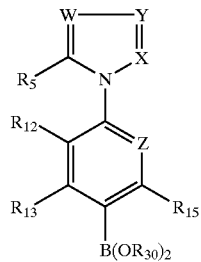

(III)

wherein W, X, Y, Z, $R_5$, $R_{12}$, $R_{13}$ and $R_{15}$ are as defined in claim 1 and $R_{30}$ is hydrogen, alkyl, or divalent lower alkylene such that $B(OR_{30})_2$ forms a cyclic borate ester; followed by reacting the resultant compound of formula (III) with a compound of formula (VI):

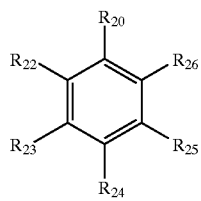

(VI)

wherein $R_{22}$, $R_{23}$, $R_{24}$, $R_{25}$ and $R_{26}$ are as defined in claim 1 and $R_{20}$ is bromine, iodine or $O-SO_2CF_3$;

(b) reacting a compound of formula (II) above with a compound of formula (V):

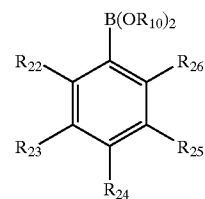

(IV)

wherein $R_{22}$, $R_{23}$, $R_{24}$, $R_{25}$, and $R_{26}$ are as defined in claim 1 and $R_{30}$ is as defined above;

(c) reacting a compound of formula (II) above with a hexaalkylstannane to form a compound of formula (V):

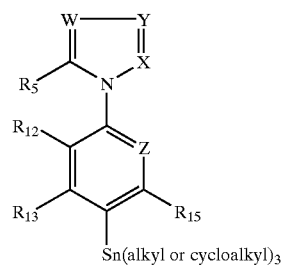

(V)

wherein W, X, Y, Z, $R_5$, $R_{12}$, $R_{13}$, and $R_{15}$ are as defined in claim 1; followed by reacting the resultant compound of formula (V) with a compound of formula (IV) above in the presence of a coupling catalyst; or (d) reacting a compound of formula (II) above with a compound of formula (VI) above in the presence of a coupling catalyst.

* * * * *